(12) United States Patent
King et al.

(10) Patent No.: US 6,511,663 B1
(45) Date of Patent: *Jan. 28, 2003

(54) TRI- AND TETRA-VALENT MONOSPECIFIC ANTIGEN-BINDING PROTEINS

(75) Inventors: David John King, Bagshot (GB); Alison Turner, Slough (GB); Nigel Robert Arnold Beeley, Thame (GB); Thomas Andrew Millican, Maidenhead (GB)

(73) Assignee: Celltech R&D Limited, Slough (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/664,377

(22) Filed: Sep. 18, 2000

Related U.S. Application Data

(63) Continuation of application No. 08/456,915, filed on Jun. 1, 1995, now abandoned, which is a division of application No. 08/232,401, filed on Apr. 25, 1994, now abandoned, which is a continuation of application No. 07/969,206, filed as application No. PCT/GB92/01047 on Jun. 11, 1992, now abandoned.

(30) Foreign Application Priority Data

Jun. 11, 1991 (GB) ............................................. 9112536

(51) Int. Cl.⁷ ...................... A61K 39/395; A61K 39/40; A61K 39/42; C07K 16/00; C12P 21/08

(52) U.S. Cl. ................................ 424/130.1; 424/133.1; 424/172.1; 424/174.1; 530/387.3; 530/387.7

(58) Field of Search ........................... 424/130.1, 133.1, 424/172.1, 174.1; 548/521; 530/367.3, 387.1, 313, 387.3, 387.7

(56) References Cited

U.S. PATENT DOCUMENTS 5,091,542 A * 2/1992 Ahlem et al. ................ 548/521
5,864,019 A * 1/1999 King et al. .............. 530/367.3

OTHER PUBLICATIONS

Karush et al. (1973) Int. Arch. Allergy Appl. Immunol. 45(1–2) abstract.*

* cited by examiner

*Primary Examiner*—Joseph K. McKane
*Assistant Examiner*—Tomas Friend
(74) *Attorney, Agent, or Firm*—Foley & Lardner

(57) ABSTRACT

The invention provides a tri- or tetra-valent monospecific antigen-binding protein comprising three or four Fab fragments bound to each other covalently by a connecting structure, which protein is not a natural immunoglobuline. Further provided are novel connecting structures for use in assembling the proteins of the invention and means for attaching a labeling or effector group thereto. The proteins of the invention are useful, for example, in the treatment and diagnosis of cancer.

8 Claims, 13 Drawing Sheets

FIG. 3  Off rate trimer Fab' and IgG B72.3

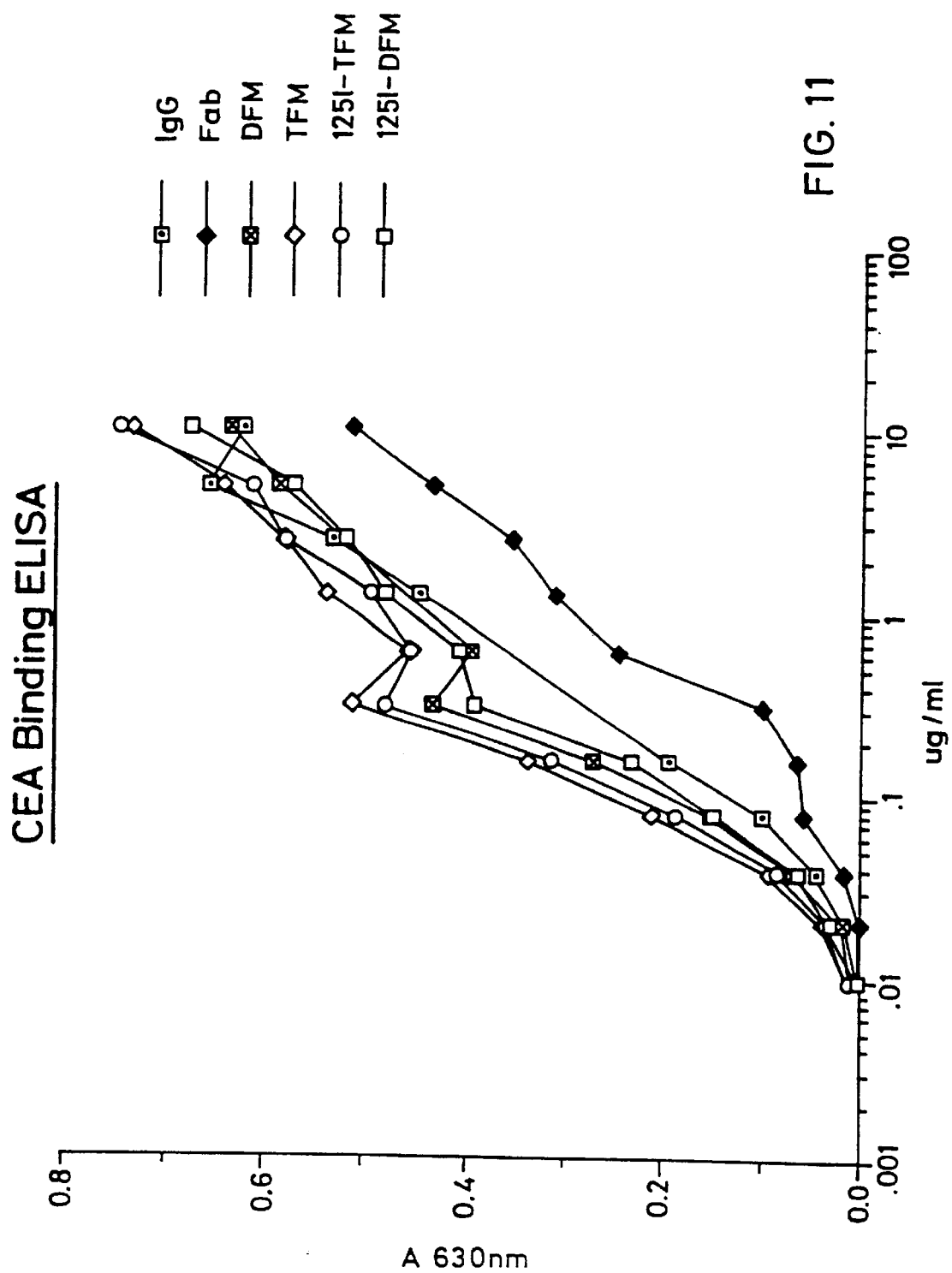

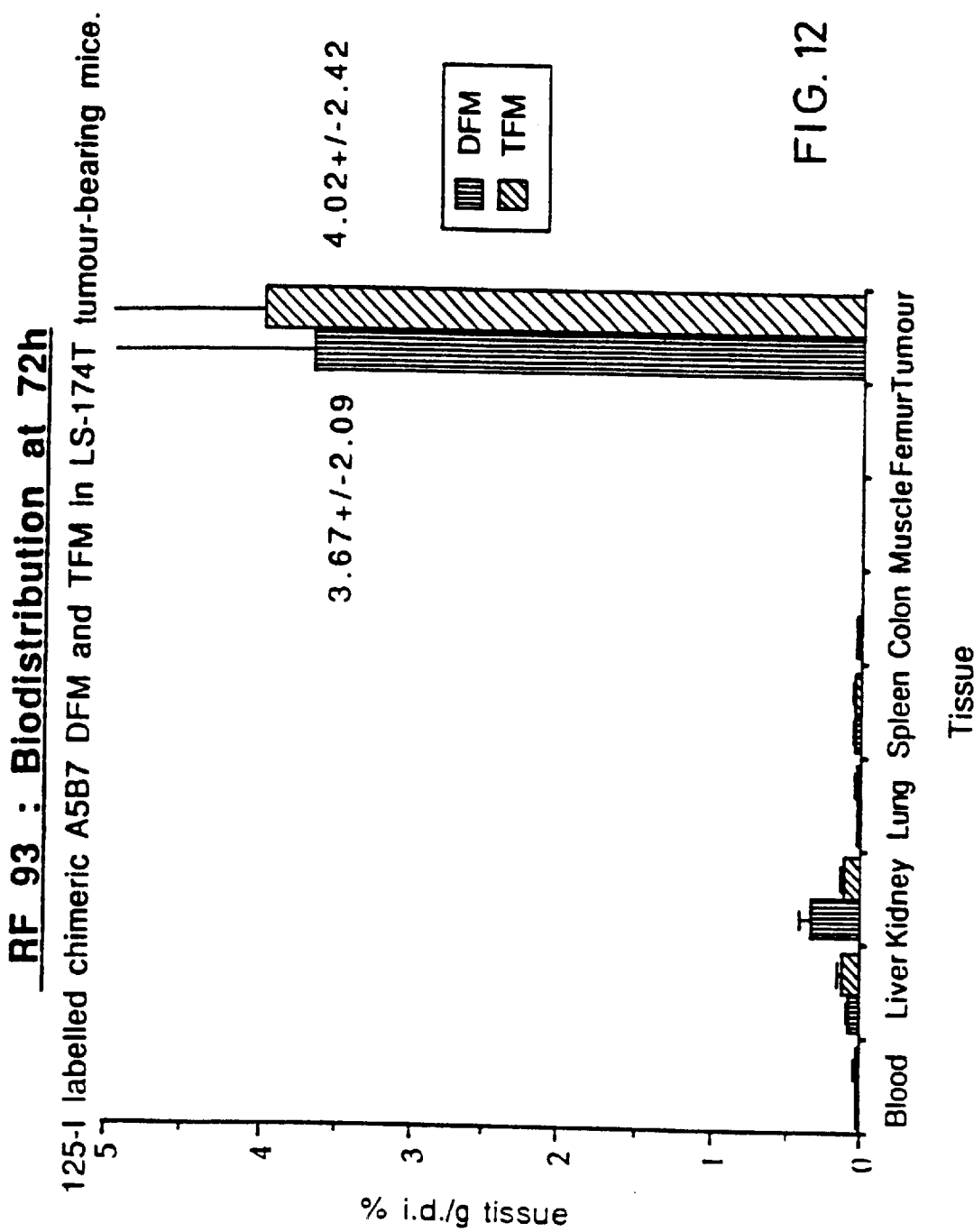

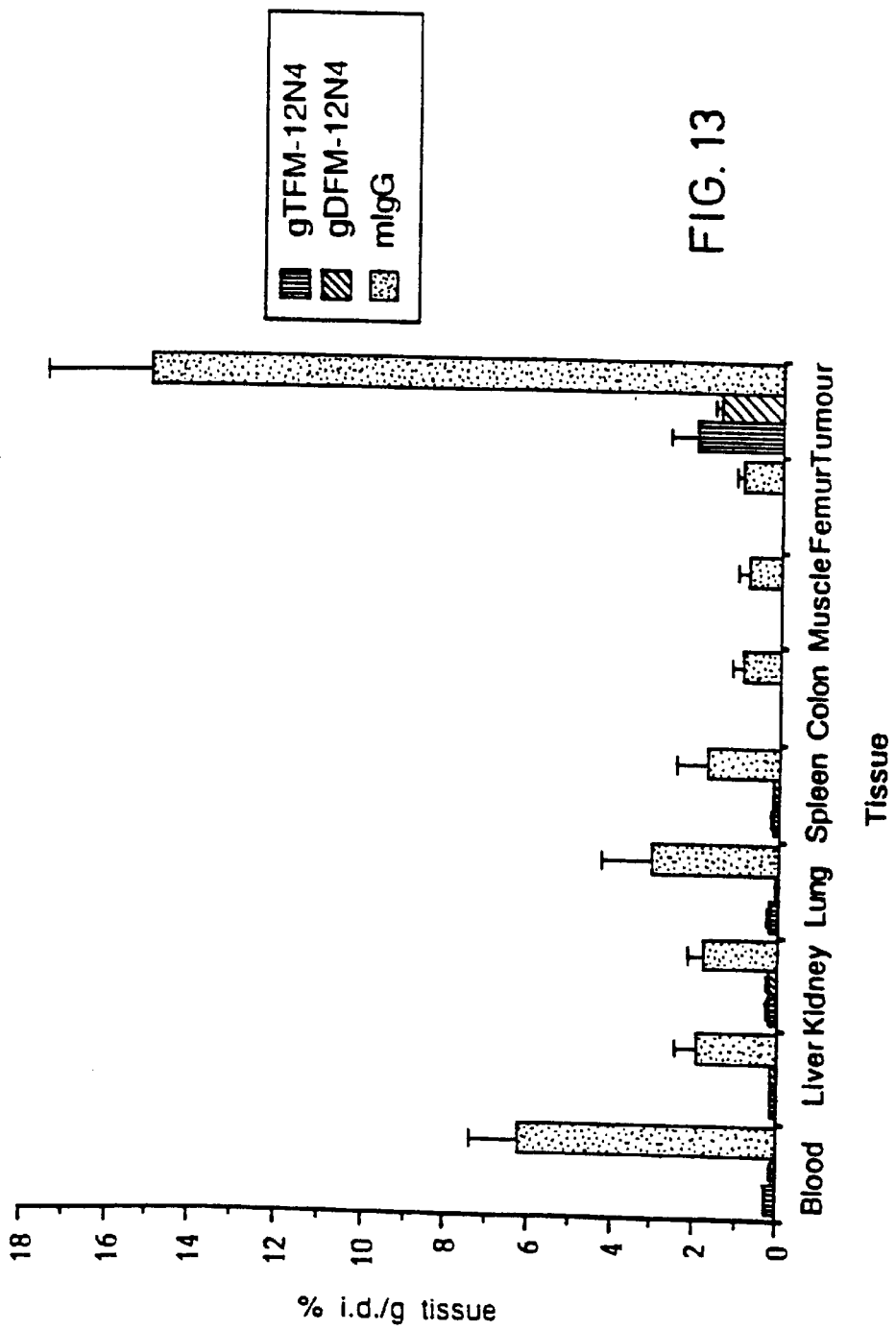

TRI- AND TETRA-VALENT MONOSPECIFIC ANTIGEN-BINDING PROTEINS

This Application is a continuation of U.S. application Ser. No. 08/456,915, filed on Jun. 1, 1995 now abandoned which is a divisional application of U.S. application Ser. No. 08/232,401, filed on Apr. 25, 1994 now abandoned which is a continuation of U.S. application Ser. No. 07/969,206, filed on Feb. 11, 1993, now abandoned, which is a national stage application of PCT/GB92/01047, filed on Jun. 11, 1992, which merits benefit of priority to U.K. Application No. 9112536.9, filed on Jun. 11, 1991.

The present invention relates to tri- and tetra-valent monospecific antigen-binding proteins and to methods for their production as well as to tri- and tetra-valent ligands for their construction. The invention relates in particular, but not exclusively, to the use of recombinant DNA technology to produce such tri- and tetra-valent monospecific antigen-binding proteins.

There has been much interest in recent years in antibodies and their fragments. It is well known that complete antibody molecules are made up of heavy chain and light chain heterodimers. For instance an IgG molecule comprises four polypeptide chains, two heavy-light chain heterodimers. Each light chain consists of two domains, the N-terminal domain being known as the variable or VL domain and the C-terminal domain being known as the constant or CL domain. Each heavy chain consists of four or five domains, depending on the class of the antibody. The N-terminal domain is known as the variable or VH domain. This is attached at its c-terminal end to the N-terminal end of the next domain, which is known as the first constant or CH1 domain. The next part of each heavy chain is known as the hinge region and this is then followed by the second, third and, in some cases, fourth constant or CH2, CH3 and CH4 domains respectively.

In an assembled antibody, the VL and VH domains associate together to form an antigen binding site. Also, the CL and CH1 domains associate together to keep one heavy chain associated with one light chain. Two heavy-light chain heterodimers associate together partly by interaction of the CH2, CH3 and, if present, CH4 domains of the two heavy chains and partly because of interaction between the hinge regions on the two heavy chains.

Each heavy chain hinge region includes at least one, and often several, cysteine residues. In the assembled antibody, the hinge regions of the heavy chains are aligned so that inter-chain disulphide bonds can be formed between the cysteine residues in the hinge regions, covalently bonding the two heavy-light chain heterodimers together. Thus, fully assembled antibodies are at least bivalent in that they have at least two antigen binding sites.

It has been known for some long time that if the disulphide bonds in an antibody's hinge region are broken by mild reduction, it is possible to produce a monovalent antibody comprising a single heavy-light chain heterodimer.

It has also been known for some long time that treatment of antibodies with certain proteolytic enzymes leads to the production of various antibody fragments. For instance, if an antibody is cleaved close to the N-terminal side of each hinge region, two antigen binding fragments (Fab) and one constant region fragment (Fc) are produced. Each Fab fragment comprises the light chain associated with a truncated heavy chain comprising only the VH and CH1 domains. The Fc portion comprises the remaining domains of the heavy chains held together by the hinge region. Alternatively, the antibody may be cleaved close to the C-terminal side of the hinge. This produces a fragment known as the F(ab')$_2$ fragment. This essentially comprises two Fab fragments but with the CH1 domains still attached to the hinge regions. Thus, the F(ab')$_2$ fragment is a bivalent fragment having the two antigen binding sites linked together by the hinge region. The F(ab')$_2$ fragment can be cleaved by reduction to produce a monovalent Fab' fragment. This can be regarded as being a Fab fragment having on it a hinge region.

It has also proved to be possible, by careful control of digestion conditions, to cleave an antibody between the VL and CL and between the VH and CH1 domains. This gives rise to two fragments known as Fv fragments. Each FV fragment comprises a VL and a VH domain associated with one another. Each Fv fragment is monovalent for antigen binding.

Studies of the amino acid sequence of individual variable domains has shown that there are three areas in each variable domain where the sequence varies considerably. These areas have been termed hypervariable regions or complementarity determining regions (CDRs). The location of these CDRs has been published [Kabat, E. A. et al., in Sequences of Proteins of Immunological Interest, US Department of Health and Human Services, NIH, USA, 1987 and Wu, T. T. and Kabat, E. A., J. Exp. Med., 132, 211–250, 1970].

Structural studies on crystallised Fv fragments and molecular modelling studies have shown that each variable domain consists of three loop regions supported on β-pleated sheet framework regions. In the case of hapten antigen binding the loop regions appear to form a pocket for receiving the antigen.

There is considerable overlap between the CDRs, as determined by sequence analysis, and the loop regions, as determined by structural analysis. However, it is generally accepted that the CDRs, possibly in combination with some extra residues present in the loop region, are primarily involved in determining the antigen binding specificity of the antibody.

In more recent years, there has been much interest in producing antibodies or their fragments by use of recombinant DNA technology. The patent literature is replete with disclosures in this area. Recombinant DNA technology has been used not only to reproduce natural antibodies but also to produce novel antibodies. For instance, it is now possible to produce chimeric antibodies, wherein the variable domains from one species are linked to constant domains from another species.

It is also possible to produce modified antibodies, in which the residues in the CDRs and, if necessary, a number of other residues in the variable domains have been changed so that a different antigen can be bound. This is a useful procedure in that it allows a specificity from, for instance, a mouse monoclonal antibody (MAb) to be created in a human antibody without altering the essentially human nature of the antibody. This has advantages where it is desired to use the antibody in vivo. A further discussion is given in W0-A-91/09967.

WO-A-90/09195 and WO-A-90/09196 relate to cross-linked antibodies and processes for their preparation. Cross linked antibody conjugates are described which have at least one non-disulphide (S—S) interchain bridge optionally containing a reporter or effector molecule. The bridge may be the residue of a homo- or hetero-functional cross-linking reagent and is located away from the antigen binding domains of the antibody. The antibody conjugates have an enhanced binding capacity, in vivo have good blood clearance and, in the presence of a tumour, high tumour: blood and tumour : bone ratios. The conjugates are of use in the diagnosis and therapy of tumours.

They may be prepared by reaction of a cross-linking reagent with an antibody or a fragment thereof. The cross-linking reagent may react either with thiol groups on the antibody molecules or with the side chains of amino acid residues such as glutamic acid, aspartic acid, lysine or tyrosine residues.

However, we have found that while cross linked antibodies as described in WO-A-90/09195 and WO-A-90/09196 have improved properties over natural immunoglobulins and in particular exhibit highly successful binding to tumour cells and good clearance from the blood, they are subject to high uptake by the kidneys and are retained in this tissue. This creates a toxicity problem, particularly when the antibody is radiolabelled for use in therapy and radioimaging. What is required is therefore an antibody molecule which retains the superior binding and clearance properties of cross-linked antibodies but which is not taken up or retained by kidney tissue and thus avoids kidney toxicity problems.

WO-A-91/03493 relates to bi- or tri-valent multispecific Fab conjugates. The conjugates which are described comprise three or four Fab' antibody fragments linked together using orthophenylenedimaleimide bridging structures. The disclosed trimeric conjugates comprise either two Fab' fragments of a first specificity and one Fab' fragment of a second specificity or three different Fab' fragments each of different specificities. Thus, the trimeric conjugates are either bi-or tri-specific. In a similar fashion, the disclosed tetrameric conjugates are at least bispecific and may be tri- or tetra-specific.

It is reported in WO-A-91/03943 that, in certain circumstances, a population of T lymphocytes can be induced to kill target cells, such as tumour cells, by treatment with a bispecific dimeric conjugate, wherein one specificity is directed at a specific antigenic structure on the T-lymphocyte population and the other specificity is directed at an antigen on the target cells. This effect is referred to as redirect cellular cytotoxicity (RCC).

The invention disclosed in WO-A-91/03493 is based on the assertion that RCC can be significantly improved by use of trimeric or tetrameric multispecific conjugates. Use of such conjugates also allows the range of T lymphocyte antigens which can be specific to be increased. It is thus essential to the invention claimed in WO-A-91/03493 that the tri- or tetra-meric conjugates should be at least bispecific.

A more detailed discussion of the invention disclosed in WO-A-91/03493 is found in Tutt, A. et al., Eur. J. Imunol., 21, 1351–1358, 1991, which confirms that it is essential, in order to enhance RCC, to use tri- or tetra-meric conjugates which are at least bispecific. However, it should be noted that nowhere in WO-A-91/03493 or Tutt et al., supra, are the clearance properties of tri- or tetra-meric Fab conjugates discussed.

It has been suggested, in our copending International Patent Specification No. WO91/19739, that multivalent antigen-binding Fv fragments will be of use in imaging or treating tumours in vivo.

A further requirement for multivalent antigen binding proteins such as those discussed above is for a cross linking molecule capable of cross linking antibody fragments together. In addition to its cross linking function, such a cross linking molecule can advantageously provide for the introduction of effector or reporter molecules to the antibody conjugate.

A number of cross-linking molecules have been described.

For example, European Patent specification No. 0446071 (Hybritech Incorporated) discloses the production of tri-functional cross linkers for use in the production of bi-specific trimeric antibody-like molecules. The application of such tris-maleimide compounds to the production of bi- or tri-specific trivalent antibody-like compounds is disclosed in European Patent Application 0453082 (Hybritech Incorporated). The clearance properties of the antibody conjugates disclosed are not referred to. A distinct drawback of the disclosed linkers is that it is difficult to attach a functional group such as a radioisotope thereto.

In particular a macrocycle cross-linking group is not easily incorporated into such linkers.

The present invention is based on the discovery that tri- and tetra-valent monospecific Fab-like proteins are particularly suitable for anti-cancer therapy. These proteins demonstrate the superior binding and clearance properties of cross-linked antibodies but are not taken up and/or retained by non-tumour tissues, including kidney tissue. In addition, the present invention provides novel linker molecules which greatly facilitate the attachment of reporter or effector groups to tri- or tetra-valent Fab-like proteins.

Therefore, according to the present invention, there is provided a tri- or tetra-valent monospecific antigen-binding protein comprising three or four Fab fragments bound to each other by a connecting structure, which protein is not a natural immunoglobulin.

The multivalent antigen-binding proteins of the invention are referred to herein as TFM (tri-Fab) and QFM (tetra-Fab). It will be understood that the expression "Fab" is used herein to include optionally modified Fab and Fab' antibody fragments derived from natural antibodies or synthesised, either chemically or by recombinant DNA technology. By "optionally modified" is meant that the Fab or Fab' fragment may contain a number of insertions, deletions or changes in the amino acid sequence, as long as the binding ability of the fragment is not adversely affected.

Preferably, in compounds according to the invention the Fab fragments are bound together covalently by the use of a single linker molecule.

Surprisingly, it has been observed that TFM and QFM have markedly superior characteristics to whole antibodies, Fab, F(ab')$_2$ and monospecific cross-linked derivatives of these fragments. While Fab, F(ab')$_2$ and their cross-linked counterparts are relatively specific for tumour cells when used in vivo, TFM and QFM show a greatly increased avidity compared therewith. At the same time, they are eliminated from the blood much more efficiently than whole antibodies. Furthermore, in contrast to previously described monospecific cross-linked Fab and F(ab')$_2$ fragments, TFM and QFM do not accumulate in the kidney. This gives rise to a decrease in undesirable side-effects, particularly where the antibody molecule is conjugated to a toxin or a radioisotope for anticancer therapy.

Preferably, the multivalent Fab-like proteins of the invention are specific for a tumour-associated antigen. Advantageously, therefore, at least the CDRs of the Fab fragments are derived from a tumour-specific monoclonal antibody (MAb). Alternatively, the CDRs may be synthetic.

It will be appreciated that any tumour-specific antigen May be targetted by the Fab-like proteins of the present invention.

The TFM or QFM compounds of the invention may be labelled by one or more reporter or effector groups, for example the types described below. The label may be incorporated on the Fab portion of the TFM or QFM molecule, and/or on the connecting structure linking the Fab portions to each other. Where the Fab portion itself is labelled, the label will generally be located such that it does not interfere with the binding site of the fragment. Methods of labelling antibodies with a reporter or effector group are well known, and are described in our published patent specifications EP 238196, EP 384624, EP 385601, WO88/05433, WO89/01475, WO89/01476 and WO90/01475. Where it is desired to include a reporter or effector group in the connecting structure, this may be achieved by reaction of the reporter. or effector group with a reactive functional group present in the connecting structure, for example in analogous fashion to that used for the labelling of the Fab fragment, or the reporter or effector group may be advantageously built in to the connecting structure, for example as described below.

Preferably, in the TFM and QFM compounds of the invention, the Fab monomers are cross-linked together by a cross-linker. The cross-linker may be any chemical capable of linking the Fab fragments together. Preferably, however, the cross-linker is a specifically designed chemical compound such as the maleimide compounds described in EP-A-0446071 and EP-A-0453082, although it will be understood that any structure having three or four functional groups reactive with any reactive amino acid found on an antibody chain may be used.

In one preference the connecting structure in the compounds of the invention is a polylysine linker. According to a second aspect of the invention, therefore, we provide a cross-linking agent of formula (1);

$R^1CH(R^2)NHCOR^3$            (1)

wherein $R^1$ is a carboxyl (—$CO_2H$) or esterified carboxyl (—$CO_2R$) group or a group —COA where A is an effector or reporter molecule attached to the —CO group either directly or via a spacer group to form a carbon-carbon, or carbon-hetero atom linkage; $R^2$ and $R^3$, which may be the same or different, is each an optionally substituted straight or branched alkylene, alkenylene or alkynylene chain [optionally interrupted by one or more —O— or —S— atoms, or —N($R^4$) (where $R^4$ is a hydrogen atom or a $C_{1-6}$ alkyl group), —N($R^4$)CO—, —CON($R^4$)—, $C_{5-8}$ cycloalkylene, $C_{6-12}$ arylene or $C_{5-10}$ heteroarylene groups) containing one or more reactive functional groups such that the total number of reactive functional groups in $R^2$ and $R^3$ together is three or more.

In the compounds of formula (1), the term "effector group" is to be understood to mean any group capable of eliciting a change in, or a response from, a biological system and which also confers this property to the compound of formula (1). The term "reporter group" is to be understood to mean any group which is detectable by analytical means in vitro and/or in vivo and which confers this property to the compound of formula (1).

Effector. groups include, for example, any physiologically active substance, antibacterial, antiviral or antifungal compound. Particular physiologically active substances include antineoplastic agents, toxins (such as enzymatically active toxins of bacterial or plant origin and fragments thereof e.g. ricin and fragments thereof), enzymes, anti-flammatory compounds and substances active as cardiovascular, e.g. fibrinolytic, and central nervous system, agents.

Particular antineoplastic agents include cytotoxic and cytostatic agents, for example alkylating agents, such as nitrogen mustards (e.g. chlorambucil, melphalan, mechlorethamine, cyclophosphamide, or uracil mustard) and derivatives thereof, triethylenephosphoramide, triethylenethiophosphoramide, busulphan, or cisplatin; antimetabolites, such as methotrexate, fluorouracil, floxuridine, cytarabine, mercaptopurine, thioguanine, fluoroacetic acid or fluorocitric acid, antibiotics, such as bleomycins (e.g. bleomycin sulphate), doxorubicin, daunorubicin, mitomycins (e.g. mitomycin C), actinomycins (e.g. dactinomycin) plicamycin, calichaemicin and derivatives thereof, or esperamicin and derivatives thereof; mitotic inhibitors, such as etoposide, vincristine or vinblastine and derivatives thereof; alkaloids, such as ellipticine; polyols such as taxicin-I or taxicin-II; hormones, such as androgens (e.g. dromostanolone or testolactone), progestins (e.g. megestrol acetate or medroxyprogesterone acetate), estrogens (e.g. dimethylstilbestrol diphosphate, polyestradiol phosphate or estramustine phosphate) or antiestrogens (e.g. tamoxifen); anthraquinones, such as mitoxantrone, ureas, such as hydroxyurea; hydrazines, such as procarbazine; or imidazoles, such as dacarbazine.

Particularly useful effector groups are calichaemicin and derivatives thereof (see for example South African Patent Specifications Nos. 85/8794, 88/8127 and 90/2839).

Suitable reporter groups include chelated metals, fluorescent compounds or compounds which may be detected by NMR or ESR spectroscopy.

Chelated metals include chelates of di- or tripositive metals having a coordination number from 2 to 8 inclusive. Particular examples of such metals include technetium (Tc), rhenium (Re), cobalt (Co), copper (Cu), gold (Au), silver (Ag), lead (Pb) bismuth (Bi), indium (In), gallium (Ga), yttrium (Y), terbium (Tb), gadolinium (Gd), and scandium (Sc). In general the metal is preferably a radionuclide. Particular radionuclides include $^{99m}Tc$, $^{186}Re$, $^{188}Re$, $^{58}Co$, $^{60}Co$, $^{67}Cu$, $^{195}Au$, $^{199}Au$, $^{110}Ag$, $^{203}Pb$, $^{206}Bi$, $^{207}Bi$, $^{111}In$, $^{67}Ga$, $^{68}Ga$, $^{88}Y$, $^{90}Y$, $^{160}Tb$, $^{153}Gd$ and $^{47}Sc$.

The chelated metal may be for example one of the above types of metal chelated with any suitable polydentate chelating agent, for example cyclic polyamines, polyethers, (e.g. crown ethers and derivatives thereof); polyamides; porphyrins; and carbocyclic derivatives.

In general, the type of chelating agent will depend on the metal in use. One particularly useful group of chelating agents in conjugates according to the invention, however, are acyclic and cyclic polyamines, especially polyaminocarboxylic acids, for example diethylenetriaminepentaacetic acid and derivatives thereof, and macrocyclic amines, e.g. cyclic tri-aza and tetra-aza derivatives; and polyamides, especially desferrioxamine and derivatives thereof.

Examples of particular macrocyclic amines include compounds of formula (2):

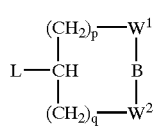

(2)

(wherein L is a substituent containing a reactive group, B is a $C_{2-4}$ alkylene chain interrupted by one or two optionally substituted nitrogen atoms; $W^1$ and $W^2$, which may be the same or different, is each an optionally substituted nitrogen atom; p is zero or an integer 1 and q is zero or an integer 1 or 2 with the proviso that when p is zero, q is an integer 1 or 2). It will be appreciated that the group L provides an attachment point for the macrocycle to the rest of the compound of formula (1). Typical groups include for example amine (—$NH_2$) containing groups. Preferred amines of formula (2) include tri-aza derivatives of formula (3):

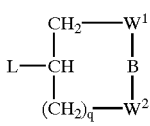

(3)

wherein $W_1$ and $W_2$ which may be the same or different is each a group —[$(CH_2)_rR^1$]— (where r is zero or an integer 1 to 6 and $R^1$ is an alkyl, alkoxyalkyl, —$CO_2H$, —$SO_3H$, —$PO_3H_2$ or aryl group) and B is a group —$CH_2(CH_2)_sN(R)(CH_2)_tCH_2$— (where s and t, which may be the same or different is each zero or an integer 1, 2 or 3; and R represents —$(CH_2)_rR^1$ where r and $R^1$ are as just described)]; and tetra-aza derivatives of formula (4);

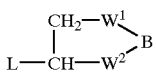

(4)

[wherein $W^1$ and $W^2$ which may be the same or different is each a group —N[$(CH_2)_rR^1$]— (as just defined) and B is a group —$CH_2(CH_2)_sN(R)CH_2(CH_2)_dN(R)(CH_2)_tCH_2$ (where d is zero or an integer 1, 2 or 3 and s, t and R are as just defined].

A particularly useful amine of formula (3) is the compound of formula (5)

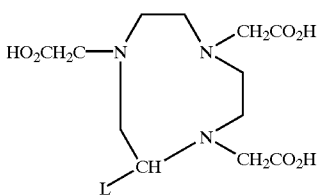

(5)

A particularly useful amine of formula (4) is the compound of formula (6):

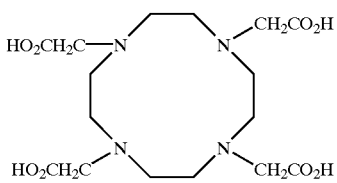

(6)

Preferred chelated metal s in conjugates according to the invention include indium chelated by a compound of formula (3), particularly the compound of formula (5); or yttrium chelated by a compound of formula (4), particularly the compound of formula (6). $^{111}$In and $^{90}$Y are particularly preferred.

The effector or reporter group may in general be attached to the remainder of the compound of formula (1) via any suitable carbon atom or heteroatom, e.g. nitrogen, oxygen, sulphur or phosphorous atom, present in it, either directly to form a compound A—COCH($R^2$)NHCO$R^3$ or indirectly to form a compound A-Sp-COCH($R^2$)NHCO$R^3$ where Sp is a spacer group attached independently to A and to —CO— group through a carbon-carbon or carbon-heteroatom linkage as just described. Suitable spacer groups include acylic or cyclic aliphatic or aromatic residues in particular alkylene [e.g. ethylene, propylene, butylene], alkoxyalklene [e.g. methoxymethylene, ethoxymethylene, ethoxyethylene], arylene [e.g. phenylene] aralkylene [e.g. phenalkylene such as phenethylene] or cycloalkylalkylene [e.g. cyclohexylmethylene]groups.

The linkage between A and the group —CO— or A and the spacer group may if desired be chosen so as to be cleavable, such as by proteolytic enzymes, for example as described in European Patent Specification No. 175617.

Esterified carboxyl (—$CO_2R$) groups represented by $R^1$ in compounds of formula (1) include those groups wherein R is an organic group, for example an acyclic aliphatic group, or an aromatic or heteroaromatic group.

Thus R may be an optionally substituted straight or branched $C_{1-2}$ alkyl, (e.g. methyl, ethyl, n-propyl, i-propyl, s-propyl, n-butyl, i-butyl, s-butyl, t-butyl), $C_{2-20}$ alkenyl, or $C_{2-20}$ alkynyl group optionally interrupted by one or more —O— or —S— atoms; or a $C_{5-8}$ cycloalkyl (e.g. cyclopentyl or cyclohexyl), $C_{5-8}$ cycloalkyl $C_{1-6}$ alkyl (e.g.cyclopentylmethyl, cyclohexylmethyl), $C_{6-12}$ aryl (e.g. optionally substituted phenyl or naphthyl) $C_{6-12}$ or $C_{1-6}$ alkyl (e.g. optionally substituted benzyl, phenethyl, or naphthylmethyl), $C_{5-10}$ heteroaryl (e.g. furanyl, pyridyl, thienyl) or $C_{5-10}$ heteroaryl $C_{1-6}$ alkyl (e.g. furanylmethyl, pyridylmethyl, or thienylmethyl) group.

The reactive functional group in compounds of formula (1) may in general be any group capable of reacting with a thiol, amino, carboxyl, hydroxyl, aldehyde, aromatic or heteroaromatic group. Aromatic groups include, for example, phenolic groups. Heteroaromatic groups include, for example, imidazolyl groups.

Thus, the reactive functional group may be, for example, a halogen atom, for example a chlorine, bromine or iodine atom, or a group selected from —SH, —S—S-Het (where Het is an optionally substituted heterocyclic group, e.g. an optionally substituted pyridyl group), —$NH_2$, hydrazine (NHH$H_2$) or a derivative thereof, [for example —N(CH$_3$) NH$_2$, —NHCON NH$_2$—NHCSNHNH$_2$ or phenyl hydrazine], haloacetamide (e.g. iodoacetamide or bromoacetamide) —NCO, —NCS, —COR$^{10}$, [where R$^{10}$is a halogen atom such as a chlorine or bromine atom, or a N$_3$, $C_{1-6}$ alkoxy, e.g. methoxy, $C_{6-12}$ aryloxy (e.g. nitrophenyloxy or dinitrophenyloxy) imidyloxy (e.g. succinimidyloxy) or imidazolyoxy group], imide, e.g. maleimide, a vinyl group of formula -Het$^1$-C(Het$^2$)=CH$_2$ (where Het$^1$ and Het 2, which may be the same or different, is each a nitrogen containing heterocyclic group, e.g. a pyridyl group or Het$^1$ is a nitrogen containing heterocyclic group and Het$^2$ is a hydrogen atom), for example a vinyl pyridyl group of formula

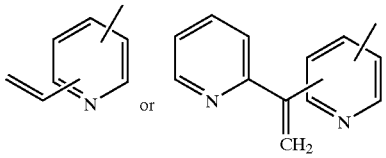

especially

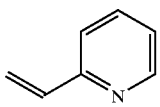

or

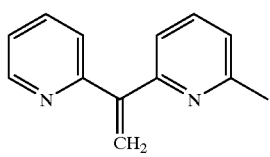

or a dione of formula

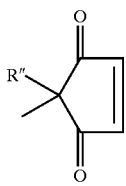

(where $R^{11}$ is a $C_{1-4}$alkyl, e.g. methyl, group).

In general, compounds of formula (1) in which the reactive functional groups are the same are preferred, although for some uses it may be preferable to have more than one type of reactive functional group. Particularly preferred functional groups are those capable of reacting with thiol groups. Groups of this type include imide (particularly maleimide), haloacetamide (particularly iodoacetamide), —SH, Het-S—S—, -Het$^1$(Het$^2$)=CH$_2$ or

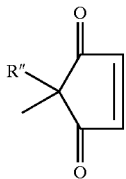

groups. Imide, especially maleimide, groups are particularly useful.

The compounds of formula (1) may contain three or more reactive functional groups, depending on their intended use.

Useful compounds include those containing three or four reactive functional groups, particularly three of four thiol-reactive groups, e.g. three or four maleimide groups, although if desired five, six, seven or eight such groups may be present.

The reactive functional groups may be distributed in the groups $R^2$ and $R^3$ is any desired way. Thus, for example, each of $R^2$ and $R^3$ may contain 1, 2, 3 or more reactive functional groups (providing the total number in both is three or more). Alternatively, the reactive functional groups may be in one of $R^2$ or $R^3$ only.

The groups $R^2$ and $R^3$ in compounds of formula (1) form a template to which the reactive functional groups are attached and may be varied within any desired size and composition. Thus, one particularly preferred, but not limiting, group of compounds of the invention has the formula 1) wherein $R^1$ is as defined above and $R^2$, which may be the same or different is each an optionally substituted straight or branched $C_{1-25}$ alkylene (e.g. $C_{1-16}$ alkylene such as methylene, ethylene, propylene, butylene, pentylene, hexylene or heptylene), $C_{2-23}$ alkenylene or $C_{2-20}$ alkynylene chains, [optionally interrupted by one or more —O— or —S— atoms, —N(R$^4$)— (where R$^4$ is a hydrogen atom or a $C_{1-6}$ alkyl group such as a methyl or ethyl group), —N(R$^4$)CO—, —CON(R$^4$)— $C_{5-8}$ cycloalkylene (e.g. cyclopentylene or cyclohexylene), $C_{6-12}$ arylene (e.g. phenylene or substituted phenylene) or $C_{5-10}$ heteroarylene (e.g. furanyl, thienyl or pyridinyl groups)] containing one or more reactive functional groups such that the total number of reactive functional groups in $R^2$ and $R^3$ together is three or more.

Optional substituents present in the groups $R^2$ and $R^3$ include carboxyl (—CO$_2$H) and esterified carboxyl (—CO$_2$R) [where R is as defined above] and amino (—NH$_2$) or substituted amino (NR$^6$R$^7$) [where R$^6$ and R$^7$, which may be the same or different, is each a hydrogen atom or a $C_{1-6}$ alkyl group, or a group —COR$^8$ where R$^8$ is as defined for $R^2$, providing that when one of R$^6$ and R$^7$ is a hydrogen atom, the other is not, and when one of R$^6$ and R$^7$ is a group —COR$^8$, the other is a hydrogen atom].

It will be appreciated that when one, or both of $R^2$ and $R^3$ contains a substituent —NHCOR$^8$ this allow for further reactive functional groups to be built into the compound of formula (1).

Particularly useful groups $R^2$ or $R^3$ may have a structure —(CH$_2$)$_m$NHCOCH(NHCOR$^8$)(CH$_2$)$_n$NHCO(CH$_2$)$_p$Z (where m, n and p, which may be the same or different is each an integer 1, 2 3 or 4 and Z is a reactive functional group as defined above.

Particularly useful groups of compounds of the invention have the formula (6):

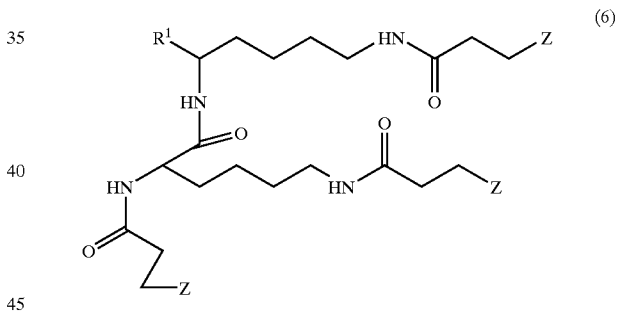

or the formula (7):

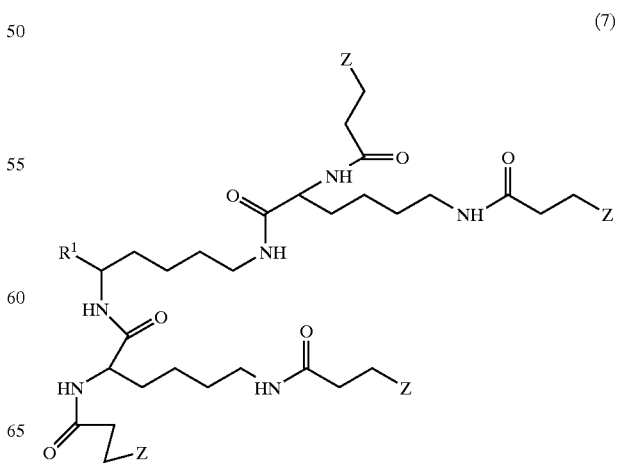

in particular the formula (8):

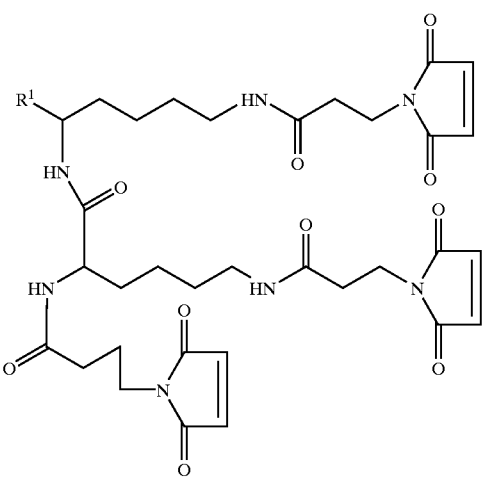

or the formula (9):

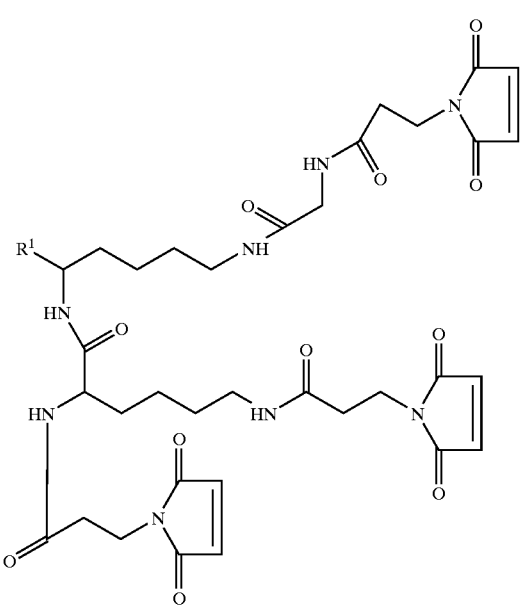

Another preferred cross-linking agent has the formula (10):

where $R^9$ is —$NH_2$ or a substituted amino group, e.g. a group —NHCOA, and A and $R^2$ are as defined for compounds of formula (1). It will be appreciated that in compounds of this type each $R^2$ group may be the same or, if desired, different to its neighbour.

The compounds of formulae (1) and (10) are of particular use for cross-linking biological materials, especially proteins, and in particular antibodies, providing the biological material(s) have one or more functional groups capable of reacting with the compound of formulae (1) or (10). The compounds are particularly useful for producing TFM and QFM compounds according to the invention.

The cross-linking reaction may be achieved using conventional processes, for example by mixing the starting materials, such as Fab fragments and the appropriate linker, in an aqueous solvent, e.g. at ambient temperature. The relative concentrations of the starting materials used will depend to a large extent on the compound of formula (1) or (10) and the number of reactive functional groups it contains, and the nature of the desired product, but generally the biological material(s), e.g. proteins such as an antibodies, e.g. a Fab fragment, will be present in excess concentration.

The compounds of formulae (1) and (10) may be prepared by a number of processes, for example as described in the examples appended hereto. In these processes reactive groups may need to be protected, when it is desired that they do not participate in a particular reaction. Conventional carboxylic acids may be esterified (for example to generate benzyl esters) and amino groups may be acylated (for example to generate benzyloxycarbonylamino groups). The protecting groups may be removed using conventional procedures, for example in the case of a benzyl ester by treatment with an acid, e.g. formic acid, and in the case of a benzyloxycarbonylamino group by treatment with a compound such as trimethylsilyl iodide.

Thus, for example, compounds of formula (1) wherein $R^1$ is a group —COA or —CO—SP-A may be prepared by reaction of a corresponding compound wherein $R^1$ is a group —$CO_2H$ or an activated derivative thereof (for example a succinimide, e.g. obtained by reaction of the acid with N-hydroxysuccinimide in the presence of dicyclohexylcarbodiimide) with the group A or SP-A, optionally in the presence of a base, in a solvent such as an ether, e.g. a cyclic ether such as tetrahydrofuran. In this reaction the starting material A or Sp-A will require a group capable of reacting with the acid-activated derivative thereof. Such groups include, for example, amino and hydroxyl groups.

Compounds of formula (1) wherein $R^1$ is a —$CO_2H$ group may be prepared by hydrolysis of the corresponding ester (—$CO_2R$), using conventional procedures, for example by hydrolysis using an acid e.g. trifluoroacetic acid, in an inert solvent such as a halogenated hydrocarbon.

In general the compounds of formula (1) in which $R^1$ is a —$CO_2R$ group may be prepared in a step-wise fashion from an esterified amino-acid starting material of formula (11):

[where Y is a side chain containing a reactive group [e.g. an amino (—$NH_2$) group] or a displaceable group (e.g. a halogen atom)] using a series of displacement or condensation reactions involving other intermediates with appropriate reactive groups using conventional procedures. The general synthetic principle may be illustrated by reference to the intermediates and examples described herein where the preparation of certain compounds according to the invention is illustrated using a known starting material. Other compounds according to the invention may be prepared using the same approach but with different starting materials and intermediates to introduce other types of groups $R^2$ and $R^3$ containing different reactive functional groups.

compounds of formula (10) may be prepared in analogous fashio using displacement and condensation reactions for example as illustrated in the intermediates and examples set out herein.

The performance of any suitable reactive functional group is always subject to the structural constraints placed upon it by the linker molecule itself. It has been found that increased linearity of the linkers facilitates the addition of a macrocycle and the chelation of an effector group.

Therefore, the invention comprises novel linkers which have a substantially linear backbone structure and are capable of accomodating a macrocycle group.

Particularly preferred are ligands of the formula:

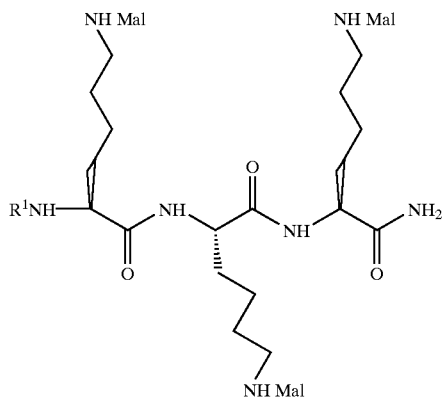

(12)

wherein $R^1$ is as described above and Mal is a maleimide group.

Preferably, the TFM or QFM of the invention is a tri- or tetra-valent monospecific antigen-binding protein comprising three or four Fab fragments bound to each other by a linker having attached thereto a macrocycle.

It will be understood that although the attachment of the macrocycle to the linkers of the invention is preferred, it is also possible to attach the macrocycle to one or more of the Fab fragments, incorporated into the multi-valent proteins of the invention. This approach is particularly preferred where the linker used does not facilitate the attachment of a macrocycle group.

Preferably, therefore, the TFM or QFM of the invention contains a radiolabel. The radiolabel is chelated by the macrocycle.

In a further preference the Fab fragment in each TFM or QFM compound according to the invention are bound to each other by a connecting structure linked to a thiol group on each Fab fragment.

Particularly preferred are tri- or tetra-valent protein constructs of the invention in which the connecting structure is one of the following linkers:

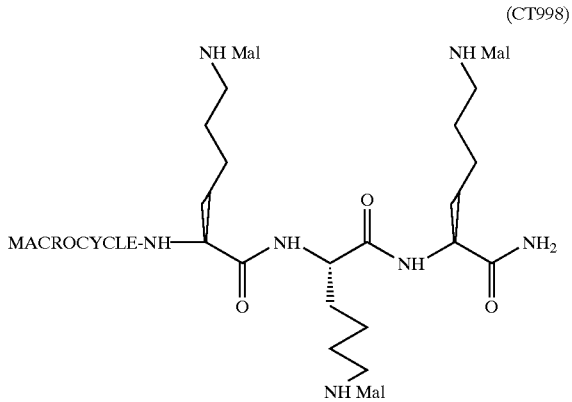

(CT998)

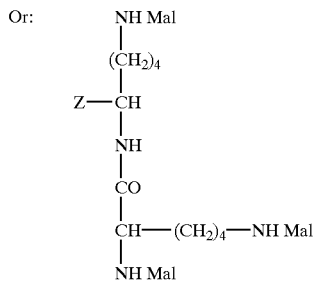

(CT557)

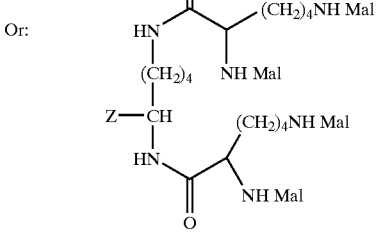

(CT558)

Naturally-occurring Fab' fragments have a number of thiol groups in the hinge region, typically two, four or even eleven. In an advantageous embodiment of the present invention, however, genetically modified Fab' fragments are used which have only a single free thiol group in the hinge region. Construction by recombinant DNA technology of such Fab' fragments, referred to as δ cys Fab' fragments, is described in our copending European patent application No. 0347433.

Decreasing the number of cysteine residues in the hinge region of a Fab-like fragment such as a Fab' advantageously decreases the possibilities of incorrect interaction between the Fab-like molecule and the linker molecule.

Normally, purified Fab' fragments produced by recombinant DNA technology are recovered with blocked hinge thiol groups. In this instance, Fab' fragments are preferably partially reduced before assembly into TFM or QFM compounds of the invention.

Preferably, the Fab' fragments are cross linked using a cross-linker of formula (1) or (10). Most preferably, the cross-linker is one of the structures depicted in the examples attached hereto. Most preferably, the linker is The tri- or tetra-valent monospecific antigen binding proteins of the invention may be used for in vivo diagnosis or therapy.

Thus the invention also includes tri- or tetra-valent monospecific antigen-binding proteins according to the invention having attached thereto diagnostically or therapeutically functional effector molecules, atoms or other species. Any of the effector or reporter groups described above may be included.

The proteins of the invention are of use for In vivo diagnostic or therapeutic purposes. Thus, the invention also includes diagnostic or therapeutic compositions for in vivo use comprising an effective amount of a protein according to the invention in combination with a pharmaceutically acceptable diluent, excipient or carrier.

The composition may comprise other active ingredients.

The composition may take any suitable form for administration, and may, in particular, be in a form suitable for parenteral administration, e.g. by injection or infusion, for example by bolus injection or continuous infusion. Where the composition is for injection or infusion it may take the form of a suspension, solution or emulsion of the protein of the invention in an oily or aqueous vehicle and it may contain formulatory agents such as suspending stabilising and/or dispensing agents. Alternatively, the compositioin may be in a dry form, for reconstitution before use with an appropriate sterile liquid.

The dose at which the protein according to the invention may be administered will depend on whether the protein is being used for diagnosis or treatment, on the nature of the condition to be diagnosed or treated, on whether the protein is being used prophylactically or to treat an exisiting condition and on the particular Fab fragment and effector or reporter group selected. Dose will also be selected according to age and condition of the patient. Thus, for example, doses in the range 0.01 to 10 mg/Kg/day may be used. Advantageously, since the compounds according to the invention are cleared rapidly from the blood, multiple dosing regimes may be used.

Moreover, the invention includes methods of diagnosis or therapy comprising administering an effective amount of a protein of the invention to a human or animal subject.

Most preferably, the method of the invention is directed to the treatment or diagnosis of cancer.

The invention further comprises the use of a tri- or tetra-valent protein as described in the preceding aspects of the invention for the treatment of an ailment, preferably cancer. Furthermore, the invention comprises the use of a tri- or tetra-valent protein according to the invention in the manufacture of a composition for the treatment of the ailment, which is preferably cancer.

The present invention is now described, by way of example only, with reference to the accompanying drawings, in which:

BRIEF DESCRIPTION OF THE DRAWINGS

FIG. 11 demonstrates the increased avidity for antigen of TFM over IgG; and

FIG. 12 and FIG. 13 show the biodistribution performance of A5B7-specific TFM.

EXAMPLES

A. Synthesis of Linkers

Figure 1:
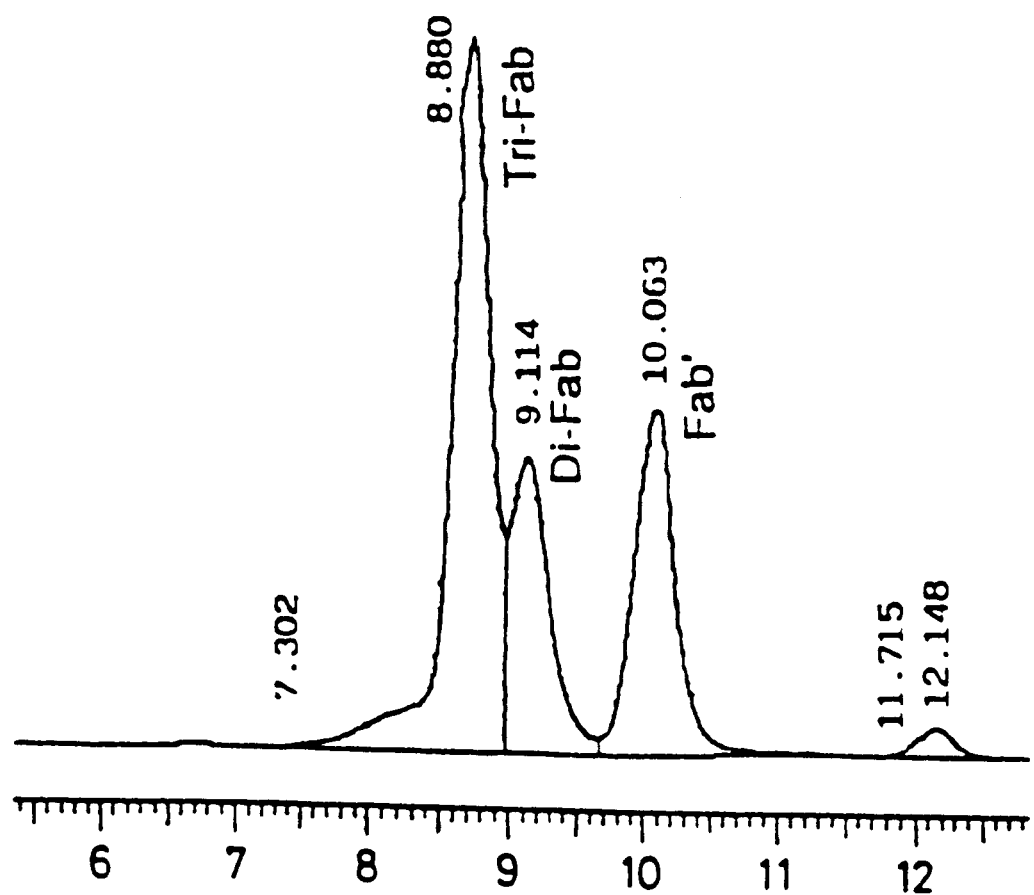
FIG. 1 is a graph showing an HPLC analysis of a cross-linking reaction as performed according to the following examples.

The following examples describe the synthesis of linkers according to the invention. In the construction of linkers, a number of intermediate compounds are used. The following abbreviations are used in the Examples:

BOC t-butoxycarbonyl
Z benzyloxycarbonyl
THF tetrahydrofuran
TFA trifluoroacetic acid
MAL

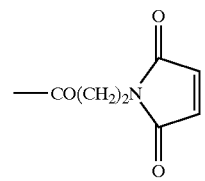

DMF dimethylformamide
MAC

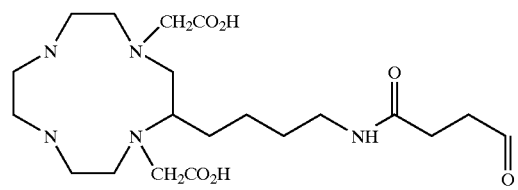

Intermediate 1

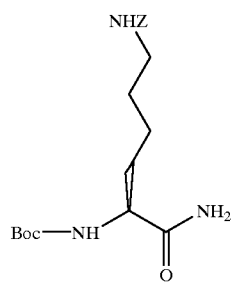

BOC-Lys(E-Z) acid (8.02 g) was dissolved in dry THF (80 ml) under $N_2$. The temperature of the reaction mixture was lowered to −20° C. and ethylchloroformate (2.29 g, 2.02 ml) and N-methylmorpholine (2.13 g, 2.31 ml) were added, maintaining the temperature at −20° C. After 30 min ammonia (16 ml of a 2M solution in methanol) was added and the reaction allowed to come to room temperature. The organic layer was added to a saturated sodium bicarbonate solution and the aqueous layer extracted with ethyl acetate, dried ($MgSO_4$) and evaporated to give Intermediate 1 (6.5 g) as a fine white solid. $^1$HNMR ($CO_3OD$) δ7.5–7.2 (m) 5H, 5.1 (s) 2H, 4.0 (m) 1H, 3.12 (t) 2H, 1.84–1.32 (m) 15H.

Intermediate 2

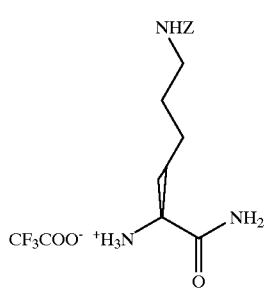

2

Intermediate 1 (4.1 g) was dissolved in a 1:1 solution (50 ml) of TFA and CH₂Cl₂ and the reaction mixture stirred at room temperature for 30 min. The solvent was evaporated and the residue triturated with ether, and dried to give Intermediate 2 (4.1 g) as a white solid. ¹HNMR (CD₃OD) δ 7.5–7 (m) 5H, 5.1 (s) 2H, 3.85 (t) 1H 3.15 (t) 2H, 1.95–1.75 (m) 2H, 1.6–1.35 (m) 4H.

Intermediate 3

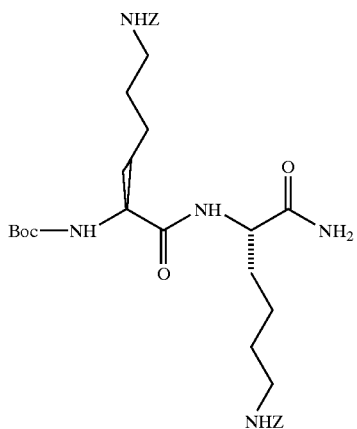

3

BOC-Lys(E-Z) acid (4.21 g), Intermediate 2 (4.15 g), ethylchloroformate (1.21 g), 1.06 ml) and n-methylmorpholine (1.12 g, 1.21 ml) were reacted together as described for Intermediate 1 to yield Intermediate 3 (7.3 g). ¹HNMR (CD₃OD) δ7.4–7.2 (m) 10H, 5.1 (s) 4H, 4.35 (q) 1H, 4.0 (q) 1H, 3.2 (t) 4H, 1.95–1.30 (m) 21H.

Intermediate 4

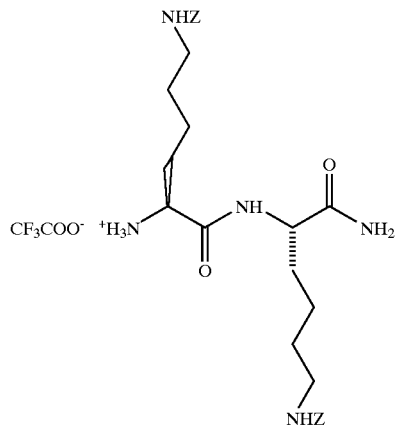

4

Intermediate 3 (4.3 g) was treated with TFA/CH₂Cl₂ (1:1, 50 ml) using the method for the preparation of Intermediate 2 to yield Intermediate 4 (4.3 g). ¹HNMR (CD₃OD) δ7.4–7.2 (m) 10H, 5.1 (s) 4H, 4.35 (t) 1H, 3.85 (t) 1H, 3.12 (q) 4H, 1.9–1.3 (m) 12H.

Intermediate 5

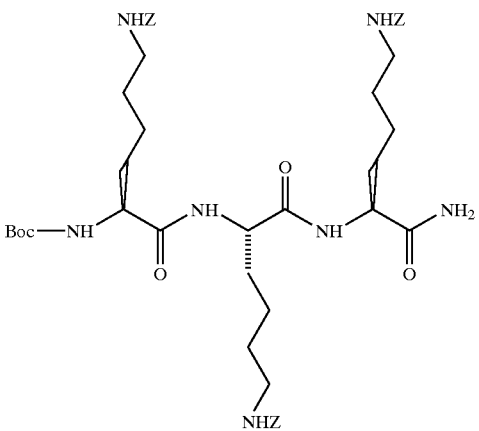

5

BOC-Lys (E-Z) acid (2.29 g), Intermediate 4 (3.76 g) ethylchloroformate (665 mg, 0.577 ml) and N-methylmorpholine (607 mg, 660 μl) were reacted together in THF (40 ml) as described for Intermediate 1 to yield Intermediate 5 (5.1 g). ¹HNMR (CD₃OD) δ7.5–7.2 (m) 15H, 5.1 (s) 6H, 4.3 (m) 2H, 4.2 (t) 1H, 3.15 (t) 6H, 1.9–1.3 (m) 27H.

Intermediate 6

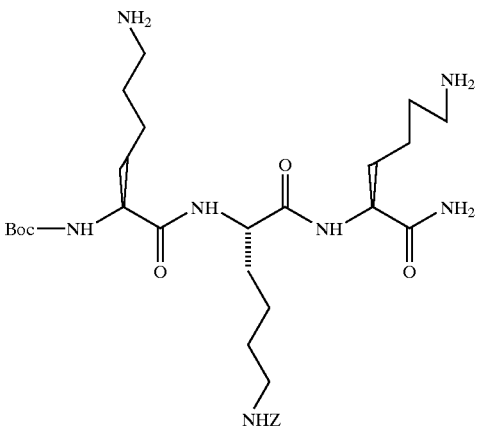

6

Intermediate 5 (4.0 g) was dissolved in methanol (100 ml) and the solution degassed for 15 min with nitrogen. The solution was then hydrogenated at room temperature using 10% Pd/C (180 mg) and a hydrogen balloon. The catalyst was filtered off and the solution concentrated in vacuo to give Intermediate 6 (2.3 g) as a pale yellow oil. ¹HNMR (CD₃OD) δ4.45 –4.25 (m) 2H, 4.0 (b.t) 1H, 2.65 (t) 6H, 2.0–1.3 (m) 27H.

Intermediate 7

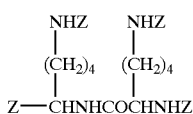

Lys (E-Z) benzyl ester (0.5 g) was dissolved in dimethylsulphoxide (3.0 ml) with slight heating. N-methylmorpholine (0.134 g) was then added followed immediately by a solution of bis-Z-Lys N-hydroxysuccinimide ester (0.754 g) in dimethylsulphoxide (3.0 ml). The reaction mixture was allowed to stand at room temperature for several hours and the reaction monitored by reverse phase HPLC [To: A-70%, C=30%, $T_{15}$: A=0, C=100%, $T_{25}$: A=0, C=100%, A=0.1/$H_2O$; C-0.1% TFA/$CH_3CN$; product eluted at 20.5 min] until complete. Intermediate 7 was then collected from the reaction solution in 0.1% TFA/$CH_3CN$:$H_2O$ and freeze dried to yield a fine white powder (750 mg).

Intermediate 8

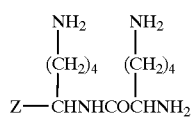

Intermediate 7 (0.25 g) was dissolved in dry $CH_2Cl_2$ (100 ml) under $N_2$ gas with stirring and then treated with trimethylsilyl iodide (10 g, 467 µl) under $N_2$ gas. The resulting pale yellow solution was left stirring at room temperature overnight, after which it had turned a dark brown colour. The $CH_2Cl_2$ was evaporated off under reduced pressure to give a dark brown residue which was dissolved in $H_2O$ (10 ml) and then extracted with ether (3×10 ml). The aqueous and ether layers were checked for the presence of free amino groups using a ninhydrin spray. The aqueous layer contained all the free amino material and was freeze dried overnight to give Intermediate 7 as a pale yellow residue.

EXAMPLE 1

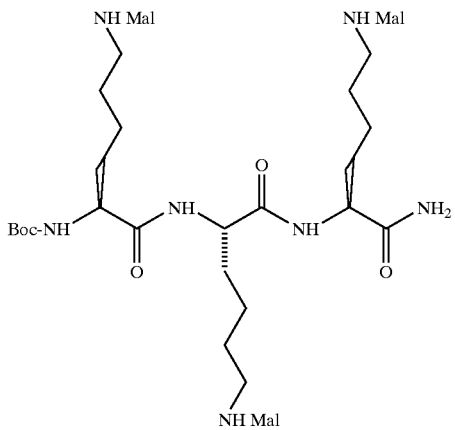

THF (10 ml) was added to dried N-maleoyl-β-alanine (444 mg) and the reaction mixture stirred at −20° C. for 10 min. Ethyl chloroformate (286 mg, 288 µl) and N-methylmorpholine (266 mg, 288 µl) were then added and the reaction mixture left at −20° C. for 30 min. Intermediate 5 (400 mg) in dry DMF (10 ml) was added maintaining the reaction mixture at −20° C. The mixture was left to come to room temperature and then purified using reverse phase HPLC (Dyanamax column C60 Å) using the following programme:

|     | A  | C  |
| --- | -- | -- |
| To  | 70 | 30 |
| $T_{20}$ | 50 | 50 |

A = 0.1% TFA/$H_2O$
C = 0.1% TFA/$CH_3CN$ to yield the desired trimaleimide compound 6 (retention time 10.7 min, 180 mg) of the Example.

HNMR ($CD_3OD$) δ6.85 (s) 6H, 4.4–4.3 (m) 2H, 4.1–4.0 (m) 1H, 3.8 (t) 6H, 3.15 (t) 6H, 2.5 (t) 6H, 1.95–1.3 (m) 27H.

EXAMPLE 2

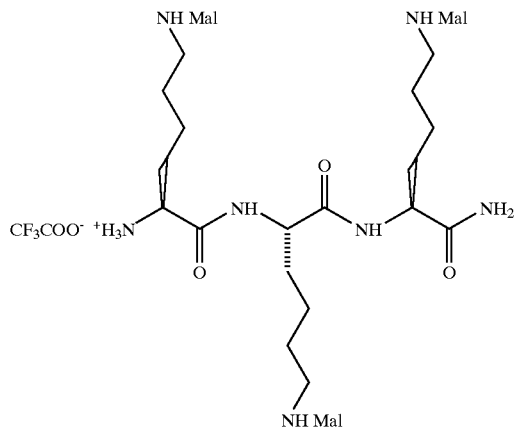

The compound of Example 1 (100 mg) was treated with TFA/$CH_2Cl_2$ (1:1, 10 ml) as described for the preparation of Intermediate2. The solvent/acid was evaporated to dryness to give an oil. Ether was added to precipitate the TFA salt, which was then freeze dried for several hours to yield the desired salt 7 (86 mg). ¹HNMR ($CD_3OD$) δ 6.8 (s) 6H, 4.4–4.2 (m) 2H, 3.95 (t) 1H, 3.7 (t) 6H, 3.2–3.1 (m) 6H, 2.45 (t) 6H, 1.95–1.3 (m) 18H.

EXAMPLE 3

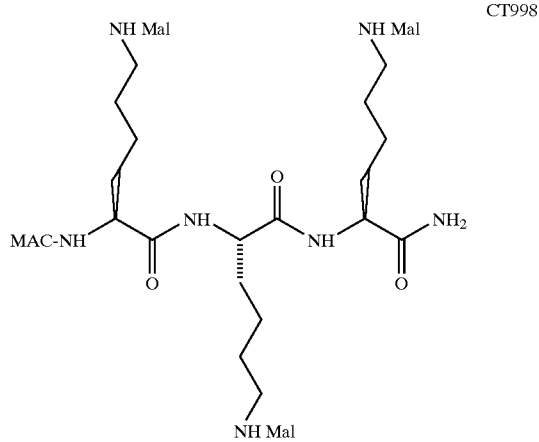

2-(4-Amino)butylperhydro-1, 4, 7, 10-tetrazadecine-1, 4, 7, 10-tetra (2-acetic acid) [Example 1(b) in International Patent Specification No. WO/89/01476] was treated with bis(p-nitrophenyl) succinate in dimethylsulphoxide in the presence of N-methylmorpholine at 20° C. for 3 h to yield the corresponding active ester β:

progress of the reaction was monitored using TLC and a ninhydrin spray. After approximately 30 min at room temperature the reaction was ninhydrin negative indicating that all free amino groups had reacted. The mixture was then

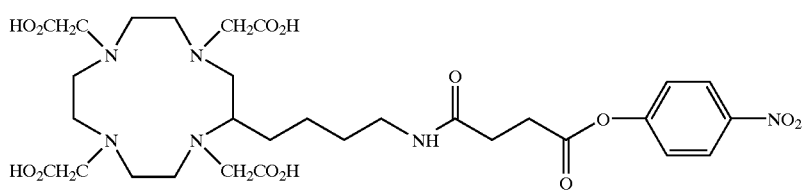

8 which was recovered as a solid (109 mg) and without further purification was dissolved in DMF(5 ml). To the resulting solution was added the compound of Example 7 (86 mg) in DMF (5 ml) followed by N-methylmorpholine (98 ml, 90 mg). The reaction mixture was left at 37° C. overnight and the desired product CT998 isolated using reverse phase HPLC (Dynamax column C60 Å) and the following programme:

purified using reverse phase HPLC and the following programme:

|  | A | C |
|---|---|---|
| To | 90 | 10 |
| $T_{20}$ | 0 | 100 |

A = 0.1% TFA/$H_2O$
C = 0.1% TFA/$CH_3CN$

The product peak eluted at approximately 14.0 min. The product pool was collected in 0.1% trifluoroacetic acid/$H_2O$: $CH_3CN$ and freeze dried overnight to give the compound of Example 4 (CT557) as a fine white material.

|  | A | C |
|---|---|---|
| To | 70 | 30 |
| $T_{20}$ | 50 | 50 |
| $T_{25}$ | 0 | 100 |

A = 0.1% TFA/$H_2O$
C = 0.1% TFA/$CH_3CN$

Retention time of CT998 −15 min Yield=11 mg $^1$HNMR ($D_2O$) δ6.8 (s) 6H, 4.3–2.4 (b.m) 59H, 2.0.1.2 (b.m) 24H. FAB MASS SPECTRA P776 M/$Z^+$=1412, 1435 ($Na^+$ adduct) 1415 ($K^+$ adduct).

EXAMPLE 4

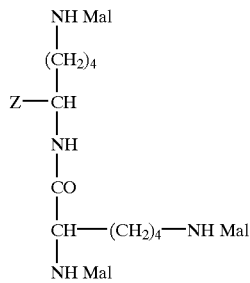

CT557

Intermediate 7 (0.2 g) was dissolved in dimethylsulphoxide and N-methylmorpholine (0.166 g) added to the solution followed by succinimidyl maleimido propionate (0.44 g) in dimethylsulphoxide (3.0 ml). On slight heating of the mixture a pale yellow solution resulted which on standing formed a white precipitate (hydrolysed propionate). The

EXAMPLE 5

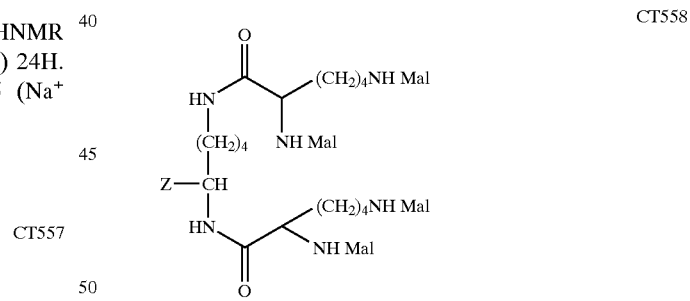

CT558

The compound of this Example was prepared using a similar series of reactions and reagents to that described for the preparation of CT557 in Example 4, except that Lys benzyl ester was used in pace of Lys(E-Z) benzyl ester to react with bis-Z-Lys N-hydroxysuccinimide ester, to yield the appropriate tetra-N-Z intermediate which was then deprotected and reacted with succinimidyl maleimido propionate as described for Example 4 to yield CT558.

B. Construction of TFM and QFM

EXAMPLE 6

The monoclonal antibody B72.3 is specific for a tumour associated glycoprotein, termed TAG72 (Colcher et al., PNAS 78, 3199–3203). Chimeric Fab' fragments of the antibody B72.3 containing a single hinge thiol group (cB72.3 Fab' δ Cys) were prepared as described in International patent specification WO89/01974 and WO89/01783. The hinge thiol group of cB72.3 Fab' δ Cys is often recovered in a blocked form and partial reduction of the cB72.3 Fab' δ Cys must be carried out to allow cross-linking to proceed. This was achieved by incubating the cB72.3 Fab' δ Cys at 3–7 mg/ml in 0.1M sodium acetate/citrate buffer pH 6.0 containing 2 mM EDTA with 4.5 mM p-mercaptoethylamine for 30 minutes at 37° C. The reducing agent was then removed by desalting on a column of Sephadex G-25 into 0.1M acetate/citrate buffer pH6 containing 2 mM EDTA. The extent of reduction was tested on an aliquot of the reduced, desalted material by titration with dithiodipyridine. The protocol typically produced approximately one thiol per cB72.3 Fab' δ Cys molecule.

Cross-linking to tri-Fab with the tri-maleimide linker CT557 was then carried out by one of two methods. In the first of these CT557 was dissolved in dry DMF and added to the freshly reduced, desalted Fab' in a five times molar excess of CT557 over Fab'. After incubation at 37° C. for 1 hour an excess of N-ethylmaleimide was added, a further ten minutes incubation at 37° C. was carried out and the mixture was then desalted on a column of Sephadex G-25 into 0.1M acetate/citrate pH6.0 containing 2 mM EDTA. This procedure generated cB72.3 Fab' δ Cys with CT557 attached. Meanwhile a further batch of freshly reduced and desalted cB72.3 Fab' δ Cys was prepared as described above and added to the Fab'-CT557 in a ratio of 2:1 (Fab':Fab'-CT557). The reaction mix was maintained overnight at 37° C and then the extent of cross-linking assessed by HPLC gel filtration and SDS-PAGE. HPLC gel filtration analysis was carried out on a DuPont Zorbax GF-250 column run at 1 ml/min in 0.2M phosphate buffer pH7.0 and SDS-PAGE was carried out as described by Laemmli (1970). Typically 30–50% of the cB72.3 Fab' δ Cys was cross-linked to tri-Fab by this method. In a second method of cross-linking with CT557, freshly reduced, desalted cB72.3 Fab' δ Cys was prepared as described above and CT557 added as a solution in dry DMF such that a molar ration of 5:1, Fab' C.T557 was achieved. The mixture was incubated at 37° C. for 1 hour or longer and the extent of cross-linking assessed by HPLC gel filtration and SDS-PAGE as described above. The extent of cross-linking to tri-Fab with this method of preparation was typically 40–60%. Typical HPLC analyses of cross-linking mixtures as shown in FIG. 1.

Tri-Fab was purified by gel filtration chromatography either using preparative HPLC on a DuPont Zorbax GF-250XL column at 3 ml/min in 0.2M phosphate buffer pH7.0 or on a 2.6 cm diameter 183 cm long column of Sephacryl S-200HR run in 0.1M acetate buffer containing 0.2M potassium chloride and 2 mM EDTA at pH 6.0.

Figure 2:
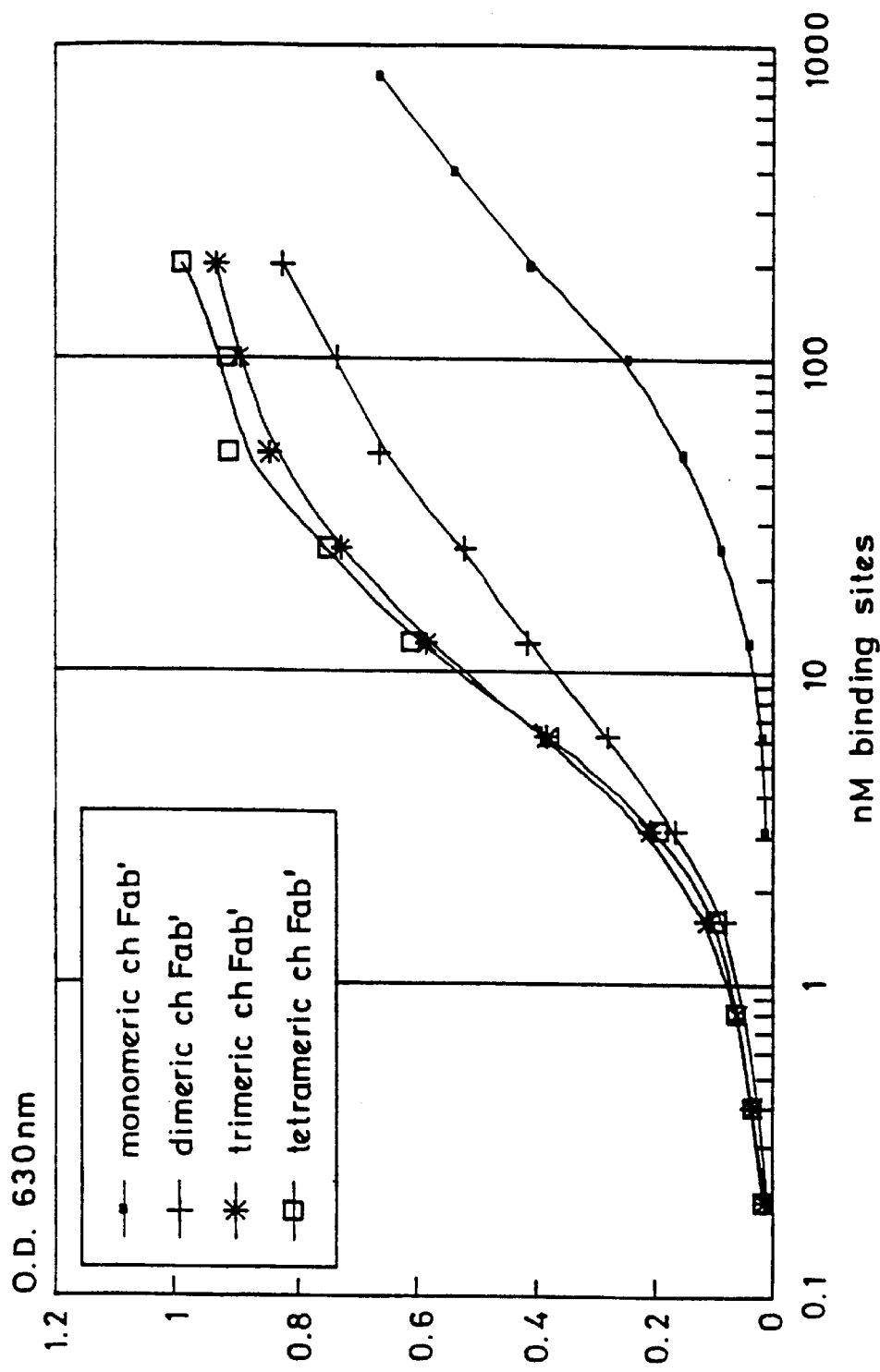
FIG. 2 shows the results of an antigen-binding ELISA comparing monomeric, dimeric, trimeric and tetrameric Fab' proteins.
Figure 3:
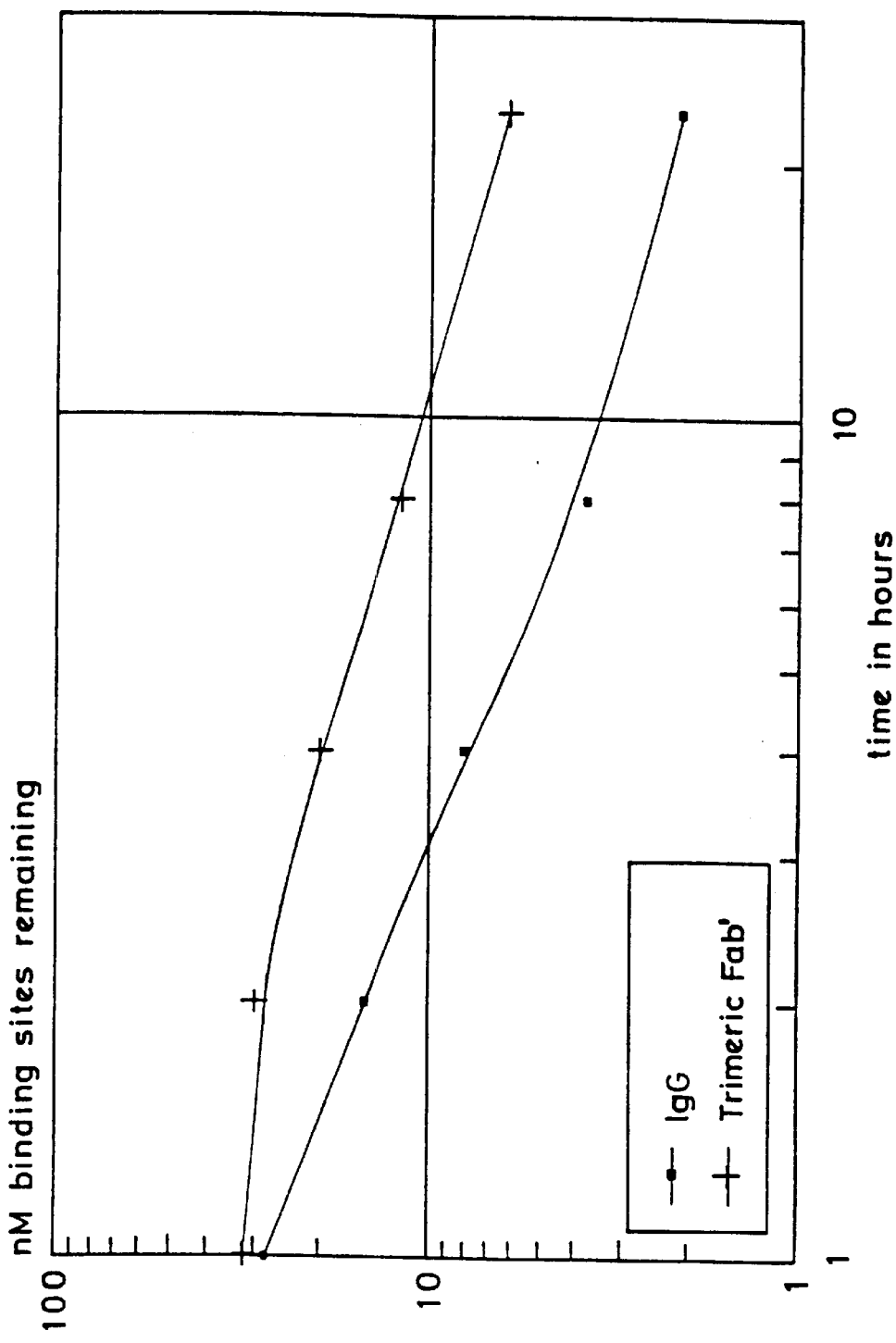
FIG. 3 is a graph showing the improved off-rate of the trimeric Fab'-like proteins (TFM) of the invention.

The antigen binding ability of tri-Fab was compared to IgG di-Fab and monomeric Fab' using a mucin binding ELISA. Titrations of monomeric, dimeric and trimeric chimeric Fab and chimeric B72.3 IgG were allowed to bind to solid-phase mucin in wells of a microtitre plate for 1 hour. Unbound antibody was washed off before addition of a goat anti-human Fab-HRPO conjugate followed by development with tetra-methylbenzidine (TMB). The signal obtained was plotted against concentrations of antibody expressed as nM binding sites. This allows a direct comparison of the efficiency of the binding site in each multimeric state. Results of the antigen binding ELISA are shown in FIG. 2. The monomeric Fab' is poor in avidity as expected whereas the di-Fab and IgG titrate in a very similar fashion also as expected. The cross-linking to tri-Fab appears to result in a 2–3 fold advantage in the ability of the binding site to bind antigen. If an increase in avidity of the molecule was achieved by cross-linking, a significant change in the off rate of the molecule would be seen. Off-rates of cB72.3 IgG and tri-Fab were compared by allowing tri-Fab and cB72.3 IgG each at 70 nM (expressed in binding sites) to bind to solid-phase mucin in wells of a microtitre plate for 16 hours. Duplicate wells were then subjected to continuous washing for 23,8,4,2 and 1 hours. Residual antibody was revealed with a goat anti-human Fab-HRPO conjugate followed by development with TMB. The signal obtained was read off standard curves of tri-Fab or IgG, and the data plotted as nM binding sites remaining in either tri-Fab of IgG format against time. FIG. 3 shows the results of this analysis. A significant improvement in off rate is seen for the tri-Fab, indicating a greatly improved ability for the molecule to remail bound to the antigen over a long time period.

cB72.3 IgG and tri-Fab (0.5 mg of each at 1 mg/ml in 0.2M phosphate buffer pH 7.0) where labelled with $^{125}I$ using Bolton Hunter reagent with standard methodology. The quality of the labelled tri-Fab and IgG were assessed by SDS-PAGE/autoradiography. There was no apparent breakdown of the tri-Fab of IgG by the labelling procedure. Groups of four female nude mice bearing subcutaneous 2–3 week old LS174T human tumour xenografts on the flank were injected i.v. in the tail vein with approximately 17 μg/9 μCi of tri-Fab and 19 μCi of IgG. Groups of animals were killed at 3 h, 24 h, 48 h and 168 h for collection of tissues which were weighed, dissolved in 7M potassium hydroxide and counted in an LKB model 1270 gamma counter. Results were expressed as mean percentage of the injected dose per gram of tissue +/− standard deviation (n=4).

Figure 4:
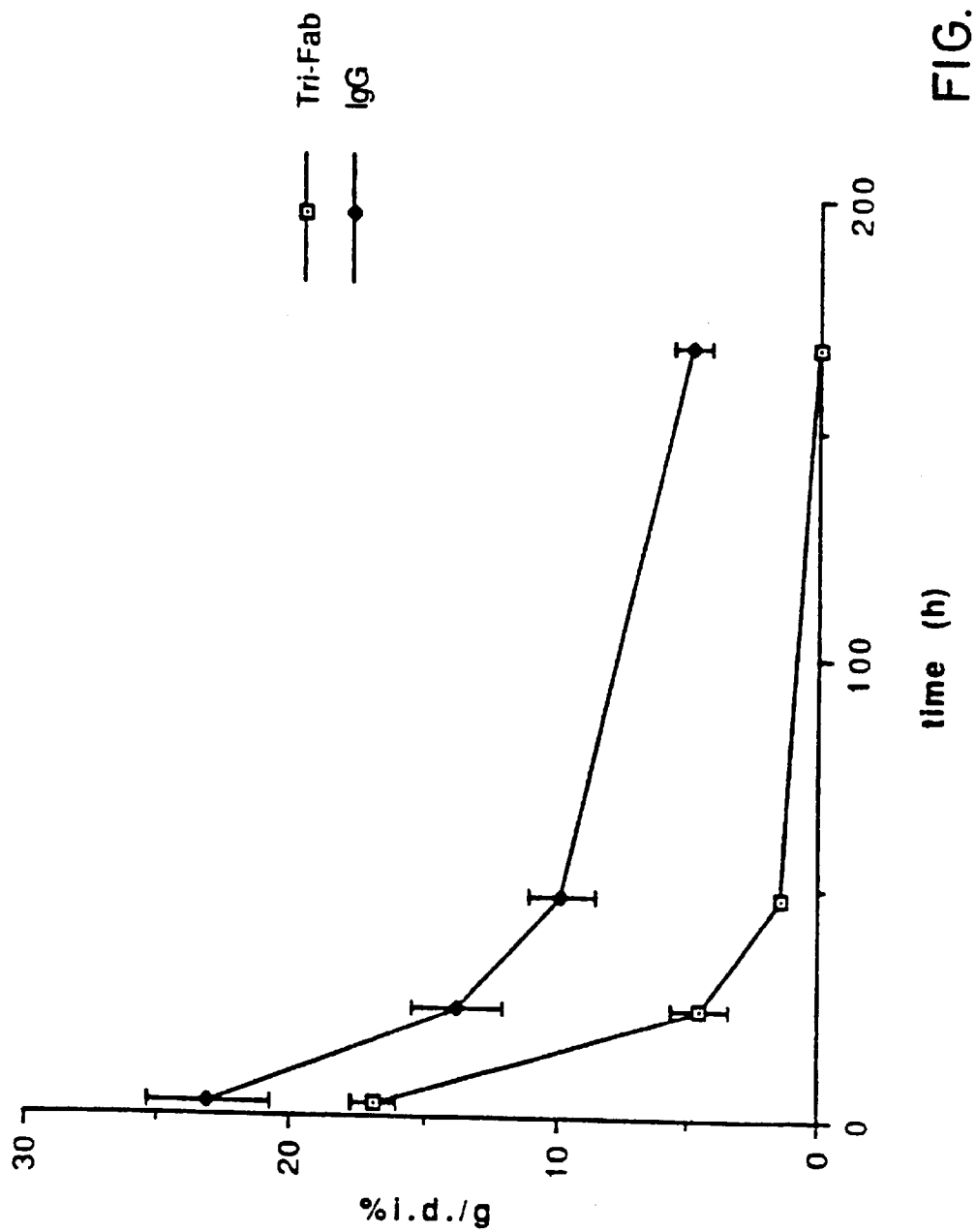
FIG. 4 is a graph showing the blood clearance performance of TFM compared to whole IgG.
Figure 5:
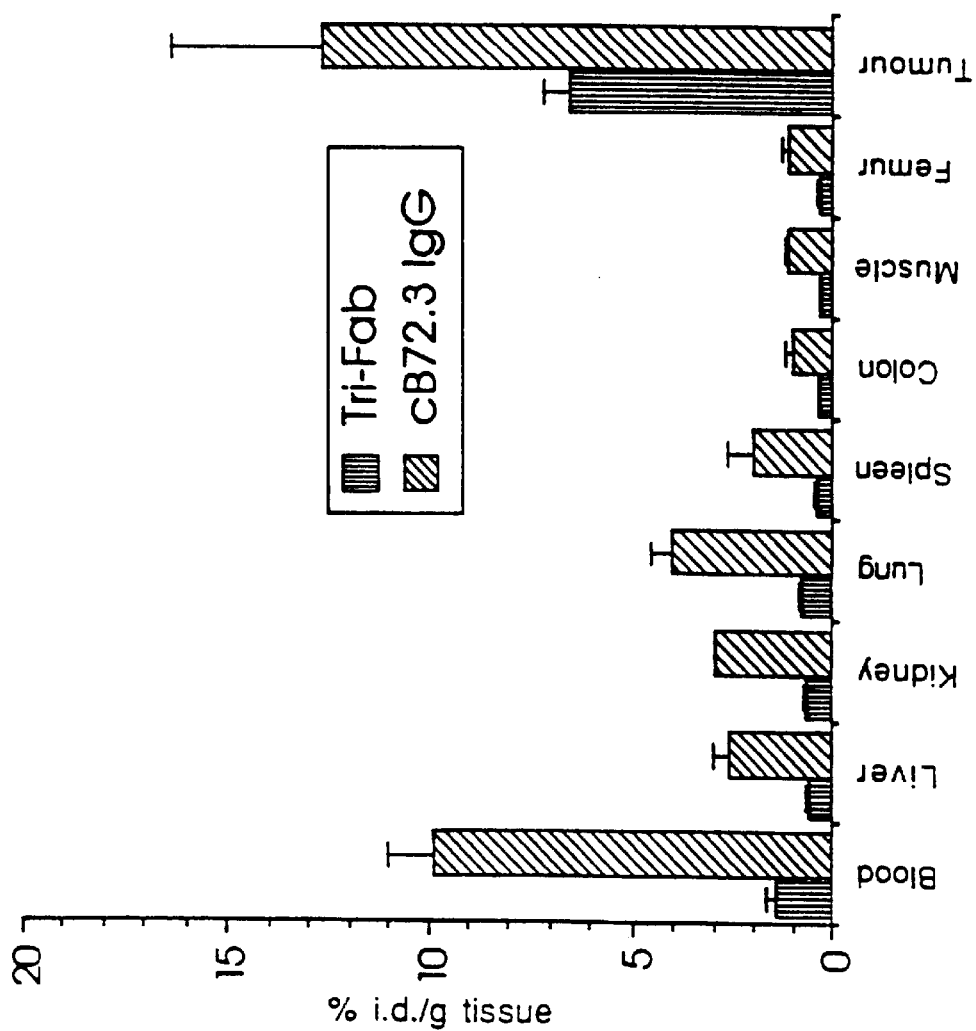
FIG. 5 compares the tissue distribution of TFM and IgG administered to tumour-bearing mice.
Figure 6:
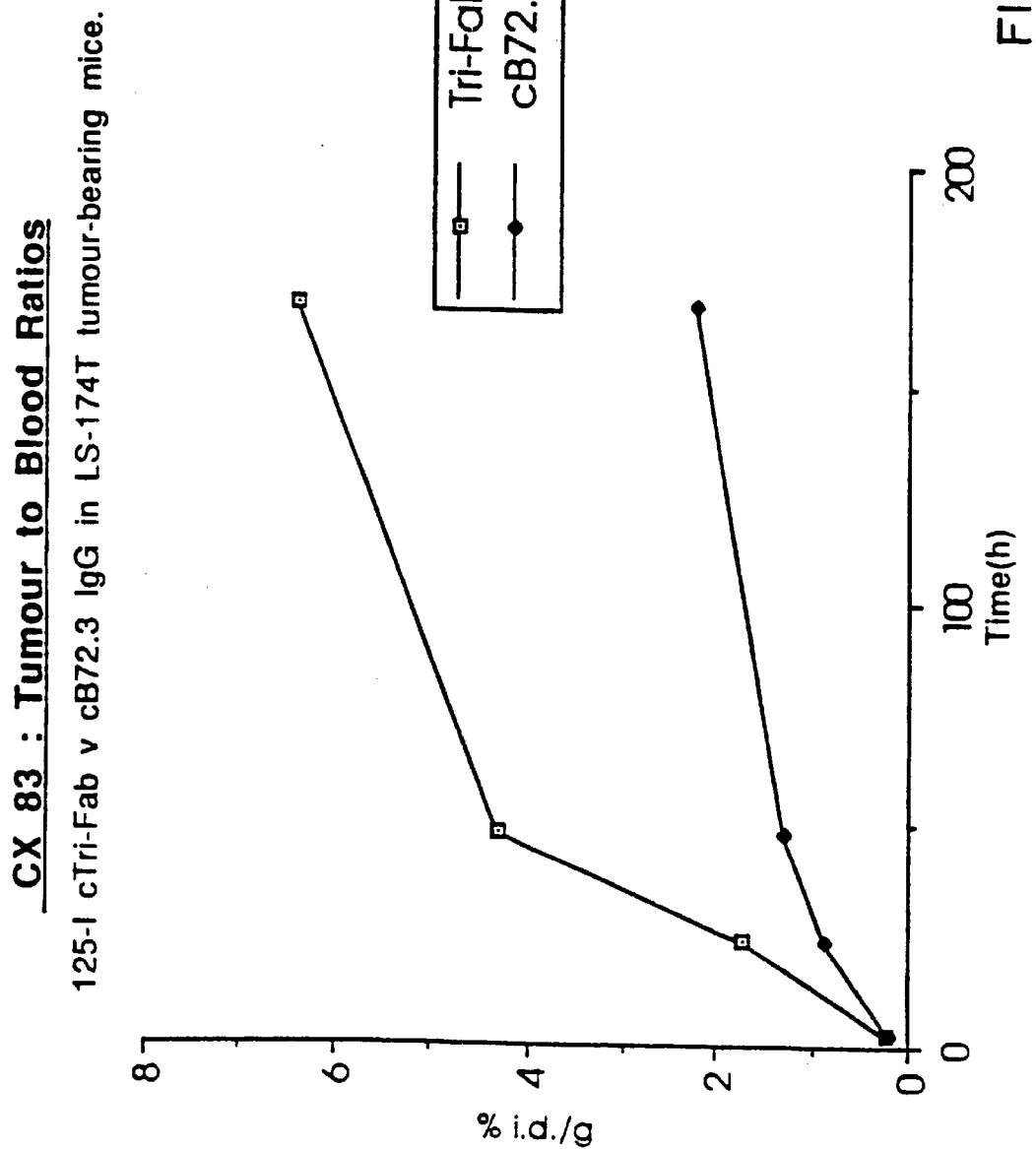
FIG. 6 depicts the tumour:blood ratio of TFM and IgG adiministered to tumour-bearing mice.

The biodistribution results for the iodinated IgG were consistent with previous experiments (King et al., 1992) Iodinated tri-Fab was found to clear significantly faster from the animals than the IgG despite the two molecules being approximately the same molecular weight (FIG. 4). The tri-Fab was able to localise well to the tumour with no significant accumulation in any other tissue (FIG. 5). consequently the tumour:blood ratios for the tri-Fab were significantly better than those seen for IgG (FIG. 6). The tumour:blood ratio is important as this means that less toxicity from blood radiation is expected for a given radiation dose to the tumour.

The biodistribution of cB72.3 tri-Fab in nude mice bearing sub-cutaneous LS174T xenograft tumours was also assessed when labelled with Y. The 12N4 macrocycle for labelling with $^{90}Y$ was attached to purified tri-Fab using a 12N4-maleimide derivative (CT77, prepared from the compound of EXAMPLE 1b in International Patent Specification WO89/01476 and the N-hydroxysuccinimide ester of N-(2-carboxyethyl)maleimide). A sample of purified tri-Fab was buffer exchanged into 0.1M sodium bicarbonate buffer pH8 containing 2 mM EDTA. Thiol groups were then introduced into the tri-Fab by reaction with a 10 fold molar excess of 2-iminothiolane over tri-Fab for 30 minutes at room temperature. The thiolated tri-Fab was then desalted into 0.1M sodium bicarbonate buffer pH8 containing 2 mM EDTA using a column of Sephadex G-25 (Pharmacia PD-10) to remove the unreacted 2-iminothiolane. The number of thiol groups present were determined by titration with dithiodipyridine. 12N4 macrocyle was then conjugated to the thiolated tri-Fab by addition of CT77 at a ten fold molar excess over the number of thiol groups present followed by incubation at 37° C. for 2 hours. The conjugate was then purified by desalting on a Sephadex G-25 column (Pharmacia PD10) into 0.1M potassium acetate pH6. Radiolabelling was achieved by the addition of $^{90}$YCl3 to the conjugate, ensuring that the buffer in the conjugate solution was sufficient to buffer the acidic $^{90}$YCl3. After incubation at 37° C. for 15 minutes the radiolabelling was quenched by the addition of 10M DTPA and the labelled tri-Fab purified by gel filtration HPLC on a DuPont Zorbax GF-250 column in 0.2M phosphate pH7. cB72.3 tri-Fab labelled with 90Y was assessed by SDS-PAGE/autoradiography. There was no apparent breakdown of the tri-Fab by the labelling procedure. Groups of four females nude mice bearing subcutaneous 2–3 week old LS174T human tumour zenografts on the flank were injected i.v. in the tail vein with approximately 3 μg/3 μCi of tri-Fab. Groups of animals were killed at 2.5 h, 24 h, 48 h and 120 h for collection of tissues which were weighed, dissolved in 7M potassium hydroxide and counted in an LKB model 1270 gamma counter. Results were expressed as mean percentage of the injected dose per gram of tissue +/− standard deviation (n=4)

Figure 7:
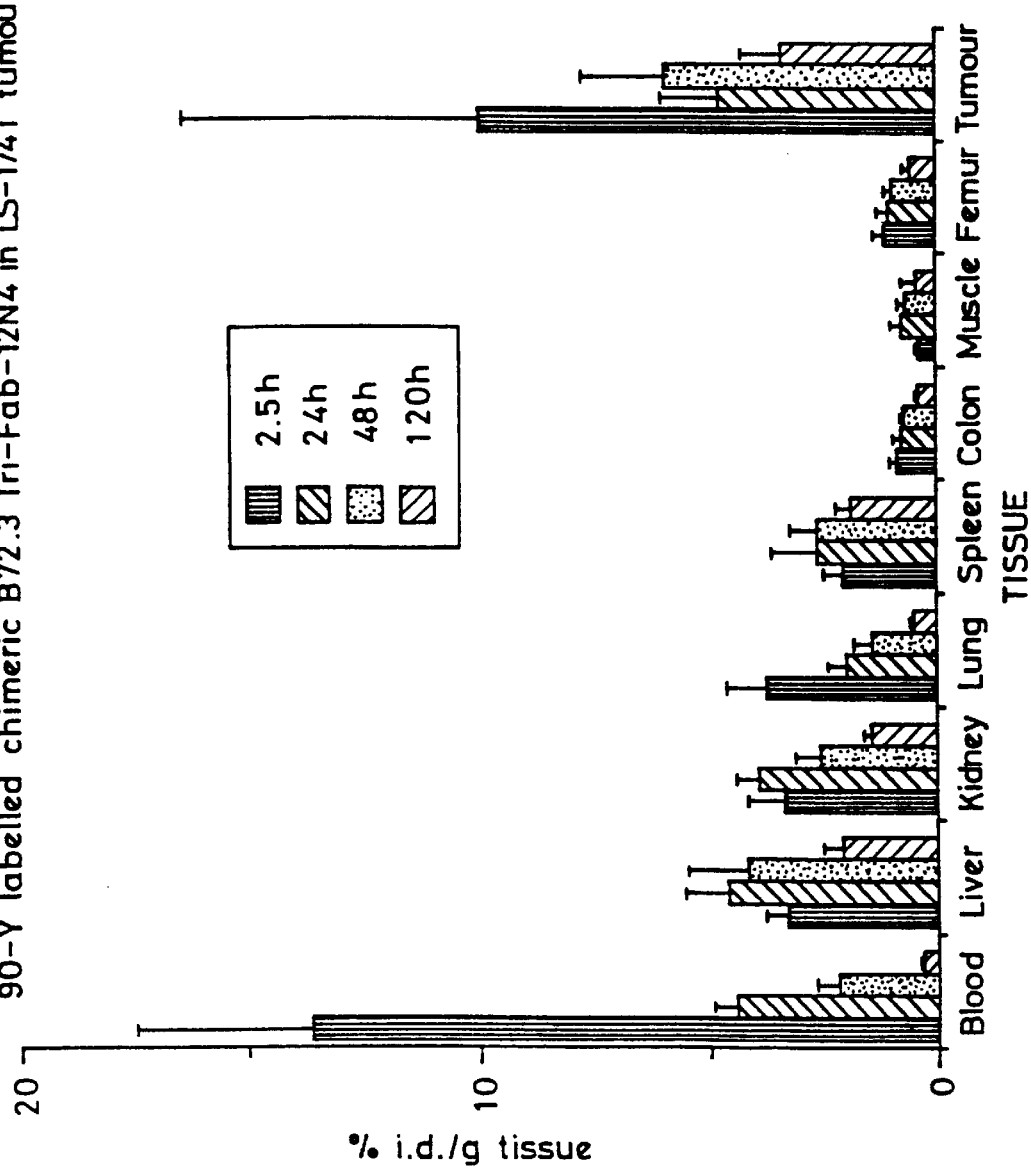
FIG. 7 shows biodistribution data similar to that shown in FIG. 5, taken at various time-points after administration of the antibody constructs.

Results of this biodistribution experiment (FIG. 7) revealed similar fast clearance of the 90Y labelled tri-Fab to that seen when labelled with 125-iodine. Good tumour localisation was seen with low levels detected in all other tissues. Importantly, low levels of activity were detected in the kidney. Retention of $^{90}$Y in the kidney when administered on other antibody fragments such as Fab and F(ab')2 has limited their usefulness, thus low kidney levels for tri-Fab represent a considerable advantage over other antibody fragments.

EXAMPLE 7 cB72.3 tetra-Fab was prepared from reduced desalted Fab' with the tetra-maleimide linker CT558 was then carried out. CT558 was dissolved in dry DMF and added to the freshly reduced, desalted Fab' in a five times molar excess of CT558 over Fab'.

Figure 8:
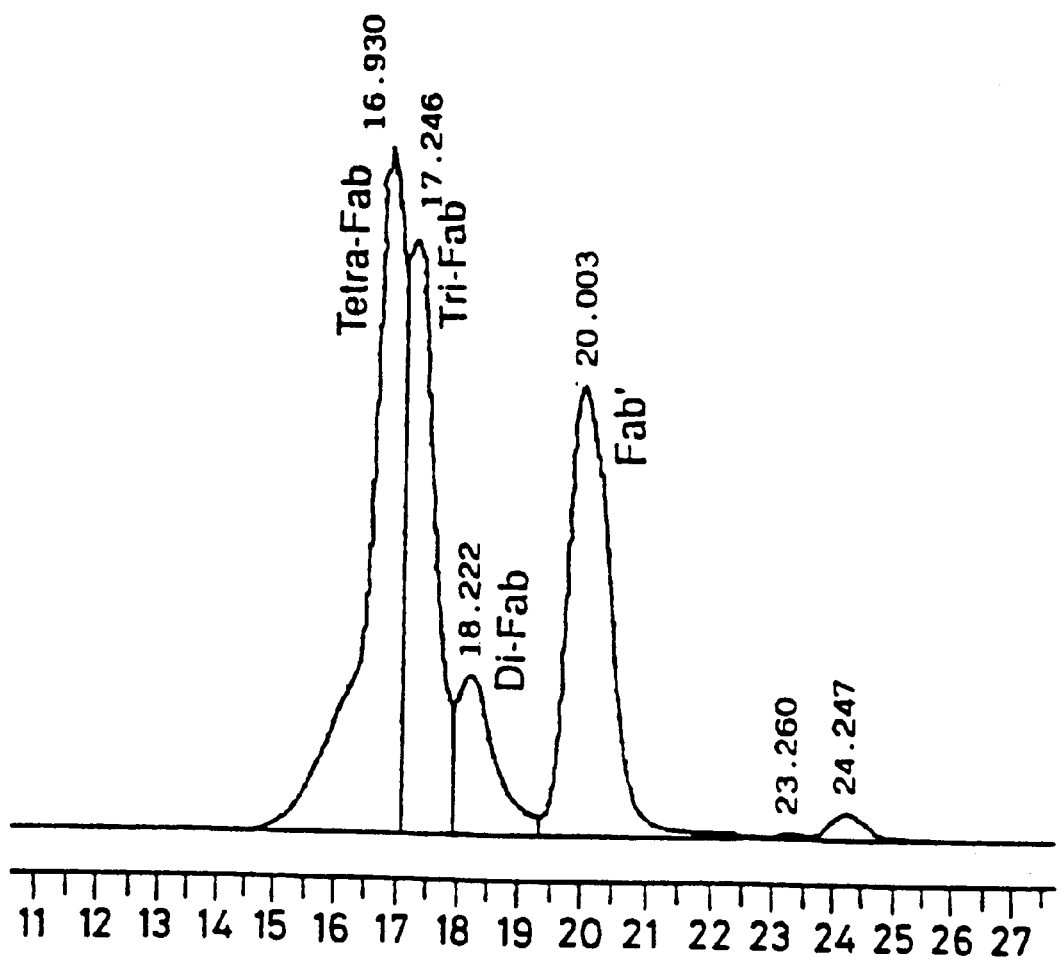
FIG. 8 is a graph showing an HPLC analysis of a cross-linking reaction for the formation of a QFM (tetra-Fab) molecule.

After incubation at 37° C. for 1 hour an excess of N-ethylmalemide was added, a further ten minutes incubation at 37° C. was carried out and the mixture was then desalted on a column of Sephadex G-25 into 0.1M acetate/citrate pH 6.0 containing 2 mM EDTa. This procedure generated cB72.3 Fab' δ Cys with CT558 attached. Meanwhile a further batch of freshly reduced and desalted cB72.3 Fab' δ Cys was prepared as described above and added to the Fab'-CT558 in a ratio of 3:1 (Fab':Fab'-CT558). The reaction mix was maintained overnight at 37° C. and then the extent of cross-linking assessed by HPLC gel filtration and SDS-PAGE as described in example 6. Typically 20–40% of the cB72.3 Fab' δ Cys was cross-linked to tetra-Fab by this method. Typical HPLC analyses of cross-linking mixtures are shown in FIG. 8. The tetra-Fab was purified by HPLC gel filtration as described for the tri-Fab in Example 6.

The antigen binding ability of tetra-Fab was measured in activity assays as described for tri-Fab in Example 6. A similar improvement in avidity over IgG was observed for the purified tetra-Fab (FIG. 2).

Purified tetra-Fab was buffer exchanged into 0.1M sodium bicarbonate buffer pH8 containing 2 mM EDTA and thiolated by incubation with a 15 fold excess of 2-iminothiolane over tetra-Fab incubated at room temperature for 30 minutes. 2-iminothiolane was then removed by desalting the thiolated tetra-Fab on a Sephadex G-25 (Pharmacia, PD-10) column in phosphate buffered saline. A 9N3 macrocycle was then conjugated to the tetra-Fab by the addition of a 10-fold excess of CT82 (prepared from the compound of example 2b in International Patent Specification WO89/01475 and the N-hydroxysuccinimide ester of N-(2-carboxyethyl)maleimide) over the number of thiol groups present (number of thiol groups determined by titration with dithiodipyridine as described above). After incubation at 37° C. overnight, an excess of N-ethylmaleimide was added and incubation continued for a further 10 minutes. The conjugated tetra-Fab was then purified by desalting into 0.1M sodium acetate pH 5.0 using a Sephadex G-25 column (Pharmacia, PD-10). The tetra-Fab conjugate was radiolabelled with 111-indium by adding 111-InCl3 directly to the purified tetra-Fab 9N3 conjugate and incubation for 30 minutes at 37° C. The labelling was quenched by the addition of DTPA to 5 mM, and the radiolabelled tetra-Fab purified by HPLC gel filtration as described above for tri-Fab.

cB72.3 tetra-Fab labelled with 111-In was assessed by SDS-pAGE/autoradiography. There was no apparent breakdown of the tetra-Fab by the labelling procedure. Groups of four female nude mice bearing subcutaneous 2–3 week old LS174T human tumour xenografts on the flank were injected i.v. in the tail vein with approximately 3.5 μg/11 μCi of tetra-Fab. Groups of animals were killed at 24 h, 48 h and 168 h for collection of tissues which were weighed, dissolved in 7M potassium hydroxide and counted in an LKB model 1270 gamma counter. Results were expressed as mean percentage of the injected dose per gram of tissue +/− standard deviation (n=4).

Figure 9:
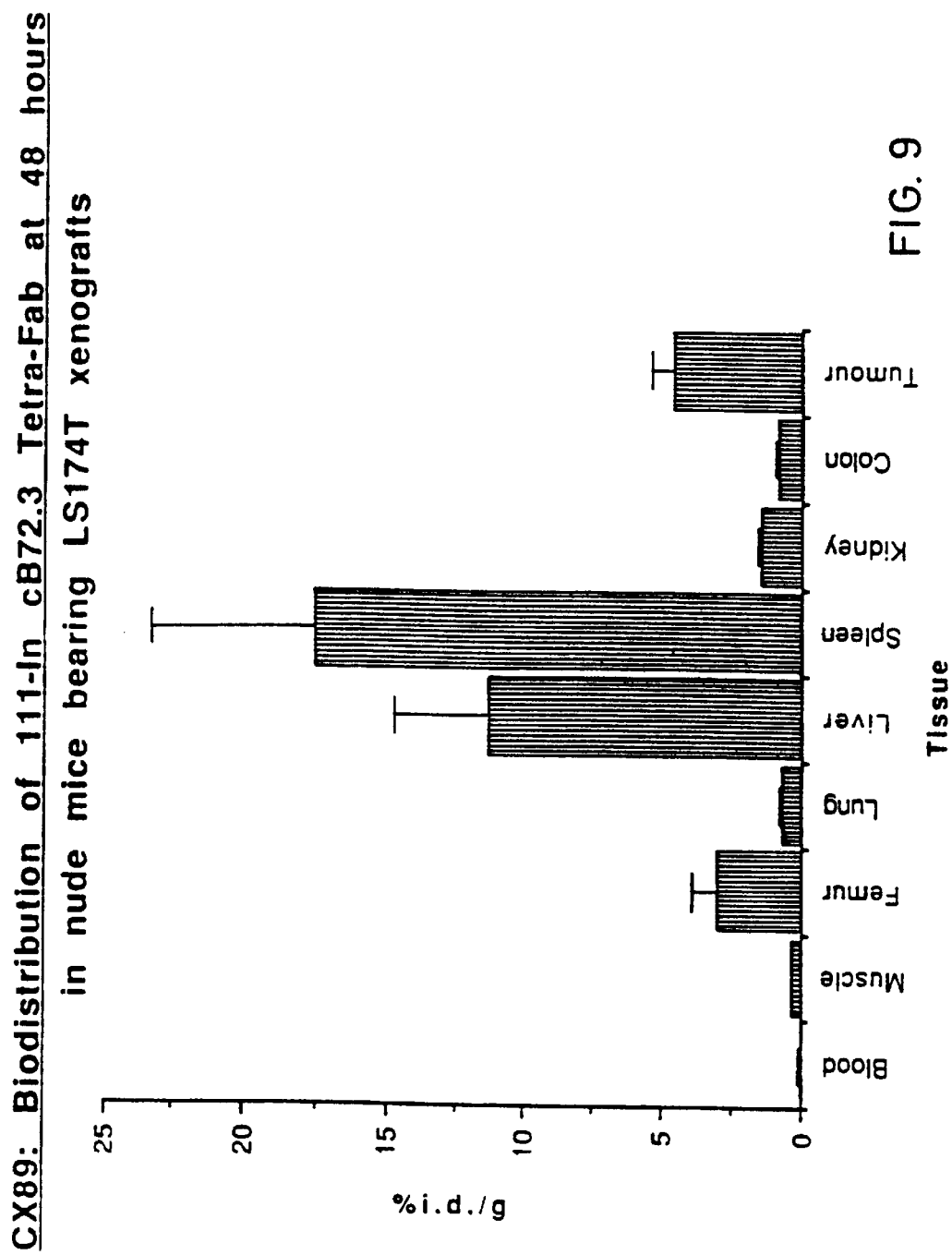
FIG. 9 shows biodistribution data for QFM constructs.

Results of this biodistribution experiment (FIG. 9) revealed fast blood clearance of the tetra-Fab and good tumour localisation, similar to that seen for tri-Fab (example 6). Again low kidney levels were observed suggesting a significant advantage for tetra-Fab, similar to that observed for tri-Fab (example 6).

Figure 10:
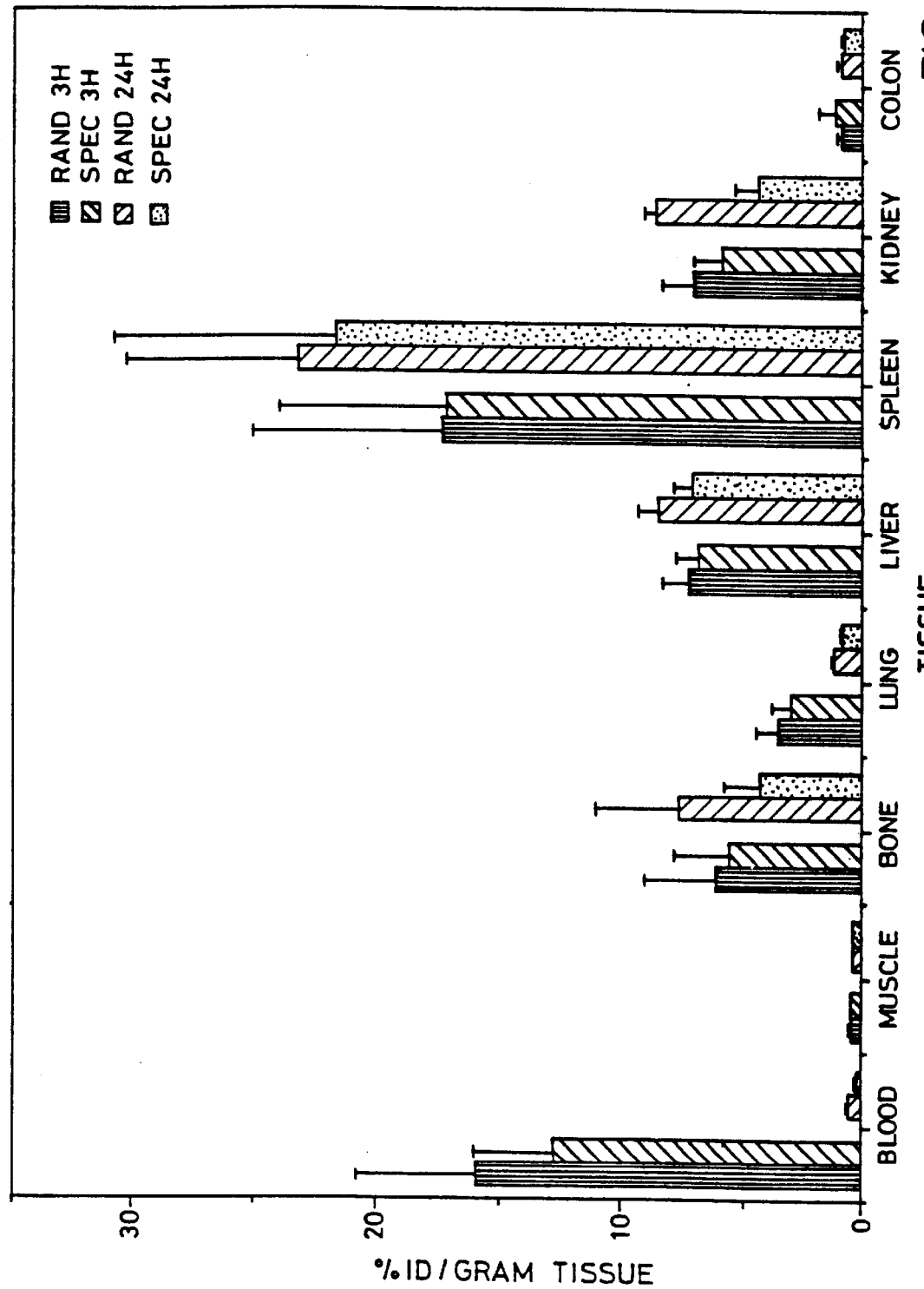
FIG. 10 compares the biodistribution of site-specific and random TFM constructs using the CT998 linker.

EXAMPLE 4 cB72.3 tri-Fab was prepared with the cross-linker CT998 by the same method described for tri-Fab with CT557 (example 6). This cross-linker contains a 12N4 macrocycle for labelling with $^{90}$Y or $^{11}$Y. Tri-Fab prepared with CT998 had equivalent activity in antigen binding assays to tri-Fab prepared with CT557. The biodistribution of cB72.3 tri-Fab (998) in mice was assessed when labelled with $^{90}$Y. $^{90}$Y labelling was achieved as described for cB72.3 tri-Fab CT77 conjugate in example 6. For cB72.3 tri-Fab (998) it was not necessary to conjugate a macrocyle as the macrocycle is already present in the cross-linker and provides a site for labelling. A biodistribution experiment was then carried out by injecting groups of 4 mice with approximately 4 μg/8 μCi of 90Y labelled cB72.3 tri-Fab (988). Groups of animals were killed at 3 h, 24 h, 48 h, 72 h and 168 h for collection of tissues which were weighed, dissolved in 7M potassium hydroxide and counted in an LKB model 1270 gamma counter. Results were expressed as mean percentage of the injected dose per gram of tissue +/− standard deviation (n-5). Results of this biodistribution experiment demonstrated that tri-Fab (988) behaved in a similar manner to cB72.3 tri-Fab made with the linker CT557. The tri-Fab(988) cleared rapidly from the circulation and was able to localise well to the tumour with no significant accumulation in any other (FIG. 10).

EXAMPLE 5

The murine monoclonal antibody ASB7 has been studied and shown to recognise the tumour associated antigen known as carcinoembryonic antigen (CEA) (Harwood et al., 1986). A mouse:human chimeric version of this antibody was produced, and the genes for a suitable cA5B7' δ Cys were constructed in an expression vector for use in NSO cells as described in Patent application WO92/01059. An NSO cell line producing cA5B7 Fab' was prepared by linearising 50 μg of plasmid DNA (pHMC30) with the enzyme FspI, electroporating into NSO cells and selecting producing cell lines as described for chimeric B72.3 (Bebbington et al. 1992).

cA5B7 Fab' 6 Cys was purified from NSO cell culture supernatant by firstly adjusting the pH of the supernatant fluid to 5 with HCl and applying to a column of protein G sepharose (Hi-trap, Pharmacia) which had been pre-equilibrated in 100 mM phosphate buffer pH 5.0 containing 150 mM sodium chloride. After loading the supernatant the column was washed with equilibration buffer and the Fab' eluted with 0.1M citric acid. Fractions containing the purified Fab' were collected directly into sufficient 1M tri to adjust the pH to between 6 and 7. The fractions containing the Fab' were pooled and concentrated by ultrafiltration. Cross-linking to cA5B7 tri-Fab with CT557 and purification of the tri-Fab was achieved by substantially the same method as described for cB72.3 Fab' δ cys in example 6. Antigen binding ability of the cA5B7 tri-Fab was compared to A5B7 IgG using a CEA binding ELISA. This was carried out substantially as described for the mucin binding ELISA in example 6, except that CEA coated plates were substituted for mucin coated plates. Results (FIG. 11) demonstrate similar improved avidity of the cA5B7 tri-Fab over IgG. The biodistribution of cA5B7 tri-Fab ove IgG. The biodistribution of cA5B7 tri-Fab was also examined in a nude mouse xenograft experiment. Approximately 3 μg/2.4 μCi of cA5B7 tri-Fab labelled with $^{125}$I (by Bolton Hunter reagent as described for cB72.3 above) was injected into groups of 4 nude mice bearing subcutaneous LS174T xenografts and the biodistribution measured at 24 h and 72 h. Results showed rapid clearance of the cA5B7 tri-Fab with localisation to the tumour (FIG. 12), demonstrating similar favourable properties as seen for cB72.3 tri-Fab.

EXAMPLE 6

A CDR grafted version of A5B7 Fab' δ Cys (gA5B7 Fab') was also produced as described in Patent application WO92/01059. Plasmid pHMC53 was constructed from pAL54 (described in WO92/01059) by removing the ampR gene and GS minigene on a BamH1-ClaI fragment and replacing it with a BamH2-ClaI fragment consisting of ampR gene and GS cDNA. This produces a vector suitable for expression in NSO cells (Bebbington et al., 1992). An NSO cell line secreting CDR grafted A5B7 Fab' δ Cys was produced using pHMC53 as described for the chimeric Fab' above.

gA5B7 Fab' was purified from NSO cell culture supernatant by firstly adjusting the pH of the supernatant fluid to 8 with 1M tris and applying to a column of protein A sepharose (Pharmacia) which had been pre-equilibrated in 100 mM boric acid buffer pH 8.0 containing 150 mM sodium chloride. After loading the supernatant the column was washed with equilibration buffer and the Fab' with 0.1M citric acid. Fractions containing the purified Fab' were collected directly into sufficient 1M tris to adjust the pH to between 6 and 7. The fractions containing the Fab' were pooled and concentrated by ultrafiltration. Cross-linking to gA5B7 tri-Fab with CT557 and purification of the tri-Fab was achieved by substantially the method as described for cB72.3 Fab' δ Cys in example 6. Again antigen binding analysis demonstrated that the gA5B7 tri-Fab was of high avidity and a biodistribution experiment of 125I labelled material carried out in a similar manner to those described above, showed similar fast blood clearance and good tumour localisation (FIG. 13).

What is claimed is:

1. A tri- or tetra-valent monospecific antigen-binding protein comprising three or four Fab fragments bound to each other by a connecting structure that is a cross-linker compound of the general formula (1):

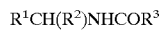

wherein $R^1$ is a carboxyl (—$CO_2$H) or esterified carboxyl (—$CO_2$R) group or a group —COA where A is an effector or reporter molecule attached to the —CO group either directly or via a spacer group to form a carbon-carbon, or carbon-hetero atom linkage; $R^2$ and $R^3$, which may be the same or different, are each an optionally substituted straight or branched alkylene, alkenylene or alkynylene chain, wherein said chain is optionally interrupted by one or more —O— or —S— atoms, or —N($R^4$), where $R^4$ is a hydrogen atom or a $C_{1-6}$ alkyl group, —N($R^4$)CO—, —CON($R^4$)—, $C_{5-8}$ cycloalkylene, $C_{6-12}$ arylene or $C_{5-10}$ heteroarylene groups, and wherein said chain contains one or more reactive functional groups such that the total number of reactive functional groups in $R^2$ and $R^3$ together is three or more; and wherein said protein is not a natural immunoglobulin.

2. An antigen-binding protein according to claim 1 which demonstrates increased antigen avidity, improved blood clearance performance and superior localisation to antigen-containing tissues when administered to an animal.

3. An antigen-binding protein according to claim 1 which is specific for a tumour-associated antigen.

4. An antigen-binding protein according to claim 3 which is specific for CEA.

5. An antigen-binding protein according to claim 3 which is specific for TAG72.

6. A method for the therapy or diagnosis of cancer, comprising the administration to a human or animal subject of an effective amount of an antigen-binding protein according to claim 1, wherein said protein is attached to a suitable therapeutic or diagnostic.

7. A method for the treatment of cancer, comprising administering an effective amount of the antigen-binding protein recited in claim 1, to a human or animal subject.

8. A method for manufacturing a composition for the treatment or diagnosis of cancer, which method comprises making the antigen-binding protein of claim 1, by binding three or four Fab fragments to a cross-linking compound of the general formula (1): $R^1CH(R^2)NHCOR^3$, wherein $R^1$ is: (1) a carboxyl (—$CO_2$H) group, (2) an esterified carboxyl (—$CO_2$R) group, or (3) a group —COA where A is an effector or reporter molecule attached to the —CO group either directly or via a spacer group to form a carbon-carbon or carbon-hetero atom linkage; and $R^2$ and $R^3$, which may be the same or different, are each an optionally substituted straight or branched alkylene, alkenylene, or alkynylene chain, wherein said chain is optionally interrupted by one or more —O—or —S—atoms, or —N($R^4$), where $R^4$ is a hydrogen atom or a $C_{1-6}$ alkyl group, —N($R^4$)CO—, —CON($R^4$)—, $C_{5-8}$ cycloalkylene, $C_{6-12}$ arylene, or $C_{5-10}$ heteroarylene group said chain contains one or more reactive functional groups such that the total number of reactive functional groups in $R^2$ and $R^3$ together is three or more.

* * * * *